US011135268B2

(12) United States Patent
Corey et al.

(10) Patent No.: US 11,135,268 B2
(45) Date of Patent: Oct. 5, 2021

(54) COMPOSITIONS, KITS, AND METHODS USING INTERLEUKIN-17C TO PROMOTE NEURAL GROWTH AND/OR NEURAL SURVIVAL

(71) Applicants: FRED HUTCHINSON CANCER RESEARCH CENTER, Seattle, WA (US); UNIVERSITY OF WASHINGTON, Seattle, WA (US)

(72) Inventors: Lawrence Corey, Mercer Island, WA (US); Jia Zhu, Kenmore, WA (US); Tao Peng, Kenmore, WA (US)

(73) Assignees: Fred Hutchinson Cancer Research Center, Seattle, WA (US); University of Washington, Seattle, WA (US)

( * ) Notice: Subject to any disclaimer, the term of this patent is extended or adjusted under 35 U.S.C. 154(b) by 0 days.

(21) Appl. No.: 15/742,415

(22) PCT Filed: Jul. 7, 2016

(86) PCT No.: PCT/US2016/041379
§ 371 (c)(1),
(2) Date: Jan. 5, 2018

(87) PCT Pub. No.: WO2017/007960
PCT Pub. Date: Jan. 12, 2017

(65) Prior Publication Data
US 2018/0193419 A1 Jul. 12, 2018

Related U.S. Application Data

(60) Provisional application No. 62/189,622, filed on Jul. 7, 2015.

(51) Int. Cl.
*A61K 38/20* (2006.01)
*C07K 14/54* (2006.01)
*A61P 31/00* (2006.01)
*A61P 25/02* (2006.01)

(52) U.S. Cl.
CPC .............. *A61K 38/20* (2013.01); *A61P 25/02* (2018.01); *A61P 31/00* (2018.01); *C07K 14/54* (2013.01)

(58) Field of Classification Search
None
See application file for complete search history.

(56) References Cited

U.S. PATENT DOCUMENTS

| 2002/0037524 | A1 | 3/2002 | Medlock et al. | |
|---|---|---|---|---|
| 2003/0003545 | A1* | 1/2003 | Ebner | A61P 15/08 435/69.5 |
| 2003/0008815 | A1* | 1/2003 | Chen | C12N 5/06 435/69.52 |
| 2006/0083713 | A1* | 4/2006 | Glasebrook | C07K 14/54 424/85.2 |

OTHER PUBLICATIONS

Oertel et al (Neurology 69: S4-9, 2007) (abstract).*
Jensen et al (Curr Opin Neurol 22: 467-474, 2009).*
Chen et al (Drug Deliv 20: 199-209, 2013).*
Interleukin 17—Wikipedia, downloaded from https://en.wikipedia.org/wiki/Interleukin_17, dated Nov. 14, 2018.*
Lidocaine Transdermal Patch—MedlinePlus, downloaded on Nov. 28, 2018 from https://medlineplus.gov/druginfo/meds/a603026.html.*
Peng et al (JEM 214: 2315-2329, 2017).*
Yan et al (Mol Ther 20: 1338-1348, 2012).*
Drake et al (J Nat Med Assoc 79: 672-673, 1987).*
Cabrera, et al., "Secreted herpes simplex virus-2 glycoprotein G modifies NGF-TrkA signaling to attract free nerve endings to the site of infection," PLoS Pathog., vol. 11, No. 1, 2015, e1004571, 22 pages.
Cattin, et al., "Macrophage-Induced Blood Vessels Guide Schwann Cell-Mediated Regeneration of Peripheral Nerves," Cell, vol. 162, No. 5, 2015, 1127-1139.
Chang, et al., Interleukin-17C promotes Th17 cell responses and autoimmune disease via interleukin-17 receptor E. Immunity, vol. 35, No. 4, 2011, pp. 611-621.
Chuong, et al., "What is the 'true' function of skin?" Exp. Dermatol., vol. 11, No. 2, 2002, pp. 159-187.
Gaffen, "Recent advances in the IL-17 cytokine family," Curr. Opin. Immunol., vol. 23, No. 5, 2011, pp. 613-619.
Gaffen, "Structure and signalling in the IL-17 receptor family," Nat. Rev. Immunol., vol. 9, No. 8, 2009, 24 pages.
Gaffen, et al., "The IL-17 cytokine family," Vitam. Horm., vol. 74, 2006, pp. 255-282.
Johnston, et al., Standard-dose and high-dose daily antiviral therapy for short episodes of genital HSV-2 reactivation: three randomised, open-label, cross-over trials, Lancet, vol. 379, No. 9816, 2012, 641-647.
Krstic, et al., "An Overview of Interleukin-17A and Interleukin-17 Receptor A Structure, Interaction and Signaling," Protein Pept. Lett., vol. 22, No. 7, 2015, pp. 570-578.
Misery, "Skin, immunity and the nervous system," Br. J. Dermatol., vol. 137, No. 6, 1997, pp. 843-850.
Moseley, et al., "Interleukin-17 family and IL-17 receptors," Cytokine Growth Factor Rev., vol. 14, No. 2, 2003, pp. 155-174.
Johnston, et al., "Keratinocyte overexpression of IL-17C promotes psoriasiform skin inflammation," J. Immunol., vol. 190, No. 5, 2013, pp. 2252-2262.
Pappu, et al., "Regulation of epithelial immunity by IL-17 family cytokines," Trends Immunol., vol. 33, No. 7, 2012, pp. 343-349.

(Continued)

*Primary Examiner* — Gregory S Emch
*Assistant Examiner* — Aditi Dutt
(74) *Attorney, Agent, or Firm* — Tanya M. Harding; C. Rachal Winger; Lee & Hayes, P.C.

(57) ABSTRACT

The present disclosure provides compositions, kits, and methods of promoting neural growth and/or neural survival using IL-17c. The compositions, kits, and methods can be used to promote neural growth and/or neural survival in a variety of conditions where such growth and survival is beneficial.

17 Claims, 28 Drawing Sheets

Specification includes a Sequence Listing.

(56) References Cited

OTHER PUBLICATIONS

Ramirez-Carrozzi, et al., "IL-17C regulates the innate immune function of epithelial cells in an autocrine manner," Nat. Immunol., vol. 12, No. 12, 2011, pp. 1159-1166.

Roizman and Whitley, "An inquiry into the molecular basis of HSV latency and reactivation," Annu. Rev. Microbiol., vol. 67, 2013, pp. 355-374.

Schiffer, et al., "Mucosal host immune response predicts the severity and duration of herpes simplex virus-2 genital tract shedding episodes," PNAS, vol. 107, No. 44, 2010, pp. 18973-18978.

Schiffer, et al., "Rapid localized spread and immunologic containment define Herpes simplex virus-2 reactivation in the human genital tract," eLife 2, e00288, 2013, 28 pages.

Shabgah, et al., "Interleukin-17 in human inflammatory diseases," Postepy Dermatol. Alergol., vol. 31, No. 4, 2014, pp. 256-261.

Song, et al., "Alterations in the microbiota drive interleukin-17C production from intestinal epithelial cells to promote tumorigenesis," Immunity, vol. 40, 2014, pp. 140-152.

Song, et al., "IL-17RE is the functional receptor for IL-17C and mediates mucosal immunity to infection with intestinal pathogens," Nat. Immunol., vol. 12, No. 12, 2011, pp. 1151-1158.

Wald, et al., "Frequent genital herpes simplex virus 2 shedding in immunocompetent women. Effect of acyclovir treatment," J. Clin. Invest., vol. 99, No. 5, 1997, pp. 1092-1097.

Iwakura, et al., "Functional Specialization of Interleukin-17 Family Members", Immunity, vol. 34, No. 2, 2011, pp. 149-162.

Li, et al., "IL-17 and VEGF Are Necessary for Efficient Corneal Nerve Regeneration", The American Journal of Pathology, vol. 178, No. 3, 2011, pp. 1106-1116.

Invitation to Pay Additional Fees dated Sep. 20, 2016 for International Application No. PCT/US2016/041379.

PCT Search Report and Written Opinion dated Nov. 22, 2016 for International Application No. PCT/US2016/041379.

* cited by examiner

FIG. 4A
FIG. 4B
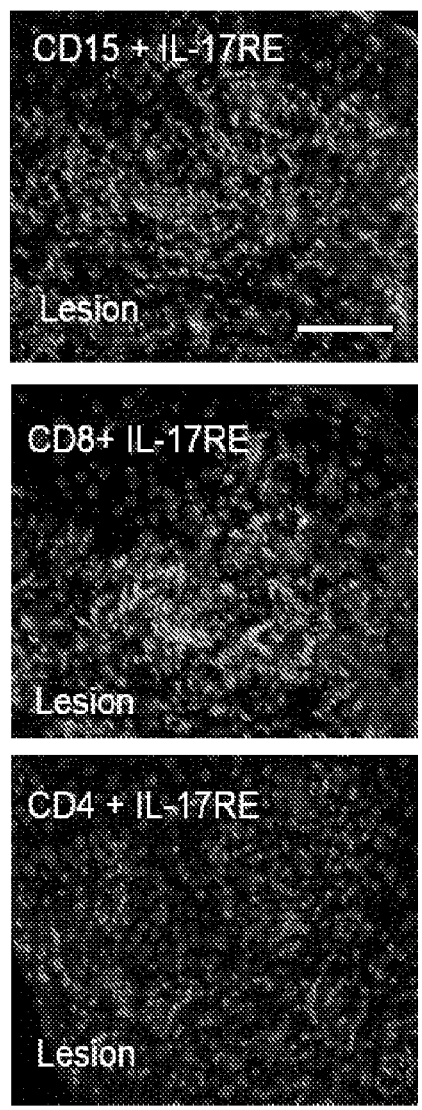
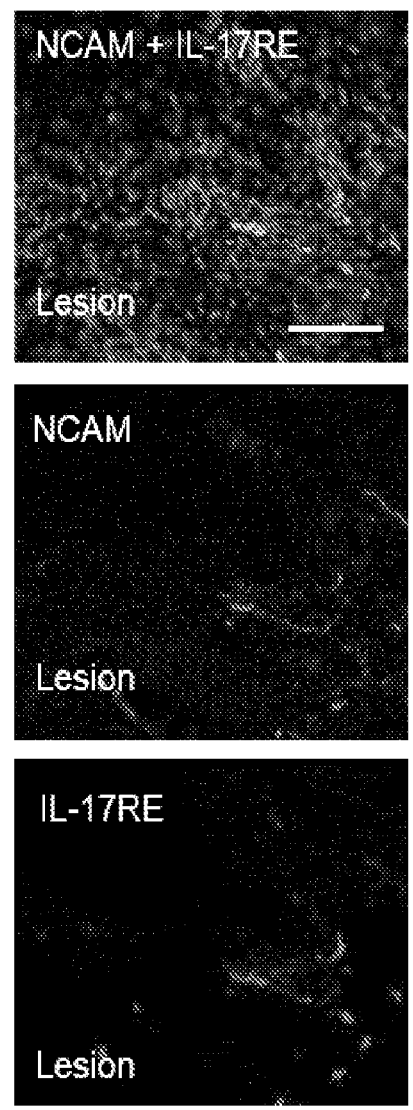

Bar: 300 micro

Bar: 300 micro

Bar: 300 micro

SEQUENCE LISTING

```
<160> NUMBER OF SEQ ID NOS: 1

<210> SEQ ID NO 1
<211> LENGTH: 197
<212> TYPE: PRT
<213> ORGANISM: Homo sapiens

<400> SEQUENCE: 1

Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
            20                  25                  30
```

```
Thr Pro His Cys Tyr Ser Ala Glu Glu Leu Pro Leu Gly Gln Ala Pro
        35                  40                  45
Pro His Leu Leu Ala Arg Gly Ala Lys Trp Gly Gln Ala Leu Pro Val
    50                  55                  60
Ala Leu Val Ser Ser Leu Glu Ala Ala Ser His Arg Gly Arg His Glu
65                  70                  75                  80
Arg Pro Ser Ala Thr Thr Gln Cys Pro Val Leu Arg Pro Glu Glu Val
                85                  90                  95
Leu Glu Ala Asp Thr His Gln Arg Ser Ile Ser Pro Trp Arg Tyr Arg
            100                 105                 110
Val Asp Thr Asp Glu Asp Arg Tyr Pro Gln Lys Leu Ala Phe Ala Glu
        115                 120                 125
Cys Leu Cys Arg Gly Cys Ile Asp Ala Arg Thr Gly Arg Glu Thr Ala
    130                 135                 140
Ala Leu Asn Ser Val Arg Leu Leu Gln Ser Leu Leu Val Leu Arg Arg
145                 150                 155                 160
Arg Pro Cys Ser Arg Asp Gly Ser Gly Leu Pro Thr Pro Gly Ala Phe
                165                 170                 175
Ala Phe His Thr Glu Phe Ile His Val Pro Val Gly Cys Thr Cys Val
            180                 185                 190
Leu Pro Arg Ser Val
        195
```

COMPOSITIONS, KITS, AND METHODS USING INTERLEUKIN-17C TO PROMOTE NEURAL GROWTH AND/OR NEURAL SURVIVAL

CROSS REFERENCE TO RELATED APPLICATIONS

This application is a U.S. National Phase Application based on International Patent Application No. PCT/US2016/041379 filed on Jul. 7, 2016, which claims priority to U.S. Provisional Patent Application No. 62/189,622 filed on Jul. 7, 2015, each of which is incorporated herein by reference in its entirety as if fully set forth herein.

STATEMENT REGARDING FEDERALLY SPONSORED RESEARCH OR DEVELOPMENT

This invention was made with government support under AI111780, AI042528, AI030731, AI093746 awarded by the National Institutes of Health. The government has certain rights in the invention.

FIELD OF THE DISCLOSURE

The present disclosure provides compositions, kits, and methods to promote neural growth and/or neural survival. The use or stimulation of the cytokine Interleukin-17c (IL-17c) in related compositions, kits, and methods are described.

BACKGROUND OF THE DISCLOSURE

There are a variety of conditions where neural growth and/or neural survival would be beneficial. For example, neurodegeneration is a damaged state of the nervous system evidenced by injured, diseased, or dysfunctional neural cells or nerves. Spinal cord injury and neurodegenerative disorders such as multiple sclerosis are examples of neurodegeneration. In the peripheral nervous system, neurodegeneration is referred to as neuropathy. Neuropathies of the peripheral nervous system are estimated to affect 20 million people in the United States. Peripheral neuropathies often cause weakness, paralysis, numbness or pain (e.g., sensations of burning, stabbing pain, tingling and/or extreme sensitivity to touch). Approximately 30% of peripheral neuropathies are caused by diabetes; 30% are idiopathic; and other causes include autoimmune disorders, tumors, heredity, nutritional imbalances, infections, chemotherapy, medications, toxins, and accidents. Promotion of neural growth and/or neural survival would be beneficial in people and animals suffering from neurodegeneration.

Neurotrophic factors are a well-known family of proteins that support the growth, survival, and maintenance of neurons. Neurotrophic factors are released by target tissue to guide axonal growth. Well-known neurotrophic factors include Nerve Growth Factor (NGF), Brain-Derived Neurotrophic Factor (BDNF), Neurotrophin-3 (NT-3), and Neurotrophin-4 (NT-4).

Interleukins are a group of cytokines that function as part of the immune system. The Interleukin-17 family of cytokines is a group of pro-inflammatory cytokines secreted by activated memory T cells that play an active role in the inflammatory response. The Interleukin-17 family of cytokines has been implicated in inflammatory diseases and autoimmune diseases.

SUMMARY OF THE DISCLOSURE

The present disclosure provides compositions, kits, and methods of promoting neural growth and/or neural survival using IL-17c. The compositions, kits, and methods can be used to promote neural growth and/or neural survival in a variety of conditions where such growth and survival is beneficial.

BRIEF DESCRIPTION OF THE FIGURES

FIGS. 4A-4F. Peripheral nervous system expression of IL-17RE, the orphan receptor for IL-17c. 4A. Nerve fibers in genital skin expressed IL-17RE. In skin biopsies obtained during recurrent HSV-2 infection, IL-17RE cells exhibited elongated fiber like shapes and were distinct from CD15+, CD8a+ and CD4+ cells. Double immunofluorescent staining with anti-IL-17RE and anti-CD15, CD8a or CD4 antibodies revealed no co-staining. Scale=50 µm. 4B. Double immunofluorescent staining with anti-NCAM and anti-IL-17RE antibodies in lesion biopsies. Nuclei stained with DAPI. Scale bar: 50 µm. 4C. Double immunofluorescent staining with anti-peripherin and anti-IL-17RE antibodies revealed expression of IL-17RE on peripherin+ nerve endings in genital 4 weeks post healed skin biopsies in epidermis (left)

and dermis (right). Nuclei stained with DAPI. Scale bar=50 µm. 4D. Single immunofluorescent staining with anti-IL-17RE in sensory neurons from human fetal DRG showed staining in both neuronal cell bodies and nerve fibers. Insets show enlarged pictures of IL-17RE expression in cell bodies (top) and axons (bottom). Scale bar=500 µm. 4E. Detection of IL-17RE RNA expression in sensory neurons in human fetal DRGs using FISH. TUBB3: tubulin beta 3 class III. Three representative images are displayed. Scale bar=50 µm. 4F. IL-17RE expression in a subset of NF200+(left panel) or peripherin+ neurons (right panel) and axons in human fetal DRG. Scale bar: 50 µm.

FIGS. 5A-5D. IL-17c expression in HSV infected human primary keratinocytes. 5A. IL-17c RNA expression in a time course of HSV infected keratinocytes. Cells were mock infected or infected with HSV-2 (HG52) in the absence or presence of acyclovir (30 µM) or with UV inactivated viruses (left panel) or such cells were infected with HSV-1 (KOS) and three HSV-1 mutants with deletion in ICP0, ICP22 and ICP8, respectively (right panel). Y-axis is fold change of RNA levels above mock infected cells; x-axis is time in hours. Gene expression for IL-17c was assayed by quantitative PCR. 5B. IL-17c protein expression in HSV-2 infected keratinocytes. Cells mock (bottom) or HSV-2 infected (top) for 7 hours at MOI of 1 and 10 were analyzed for IL-17c expression by immunofluorescent staining with an anti-IL-17c antibody. Nuclei stained with DAPI. Graph is quantification of staining as the percentage of IL-17c expressing cells. Error bars represent one standard deviation from the mean of three replicates. 5C. HSV infection and bacterial TLR agonists independently induce IL-17c expression in primary keratinocytes. A TLR2 neutralizing antibody was added to the cells one hour before infection or peptidoglycan (PGN) treatment. For combination of HSV infection and PGN treatment, cells were infected with KOS at MOI of 1 for 3 hours and were then treated with PGN (2 ug/mL) for an additional 3 hours (left panel). For combination of HSV infection and flagellin treatment, cells were mock infected or infected with ICP8mu for 7 hours, or untreated or treated with flagellin (100 ng/ml) for 1 hour or infected with ICP8mu for 6 hours and then treated with flagellin for 1 hour (right panel). Error bars represent one standard deviation from the mean of three biological replicates. Gene expression for IL-17c was assayed by quantitative PCR. 5D. NF-κB and IRF-3 mediated IL-17c induction during HSV infection of human primary keratinocytes. Cells were transfected with control siRNA (siRNA_ctrl) or siRNA for NF-κB, IRF1, IRF-3 or IRF7 for 48 hours and then mock infected or infected with KOS for 3 and 6 hours. Gene expression for IL-17c was assayed by quantitative PCR. Error bars represent one standard deviation from the mean of three biological replicates.

Figure 6A:
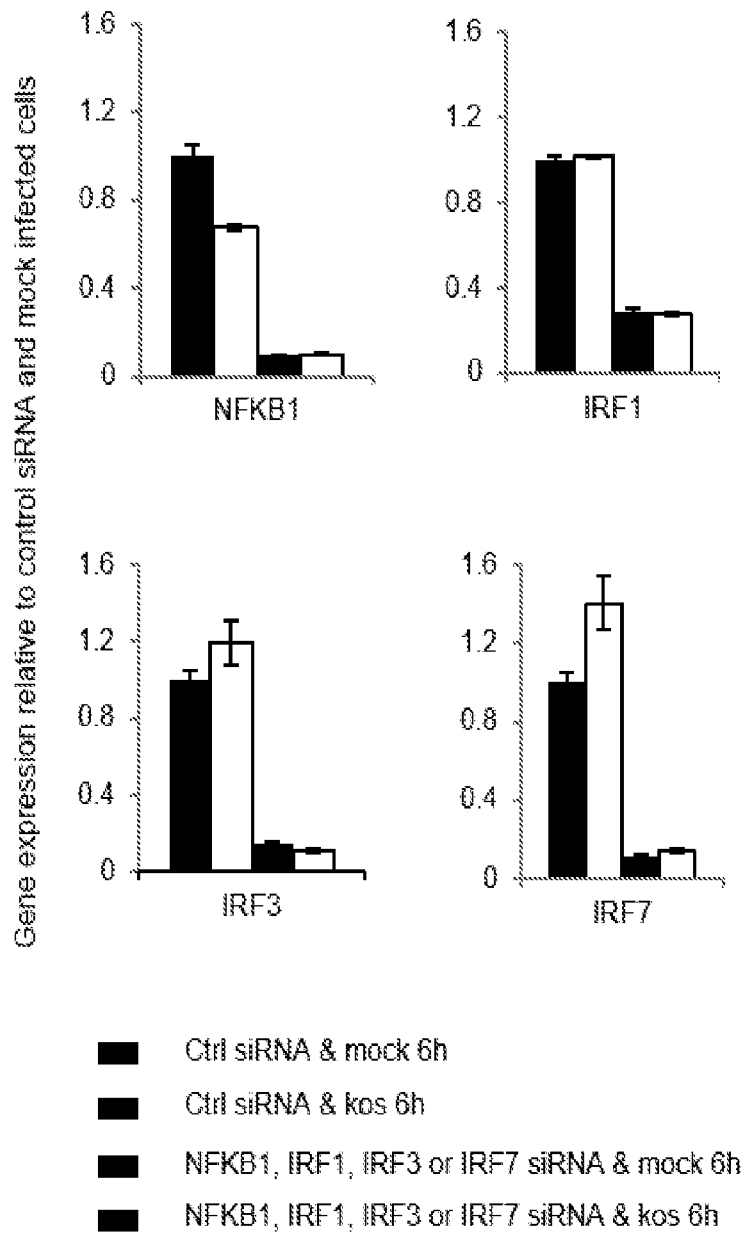
Figure 6B:
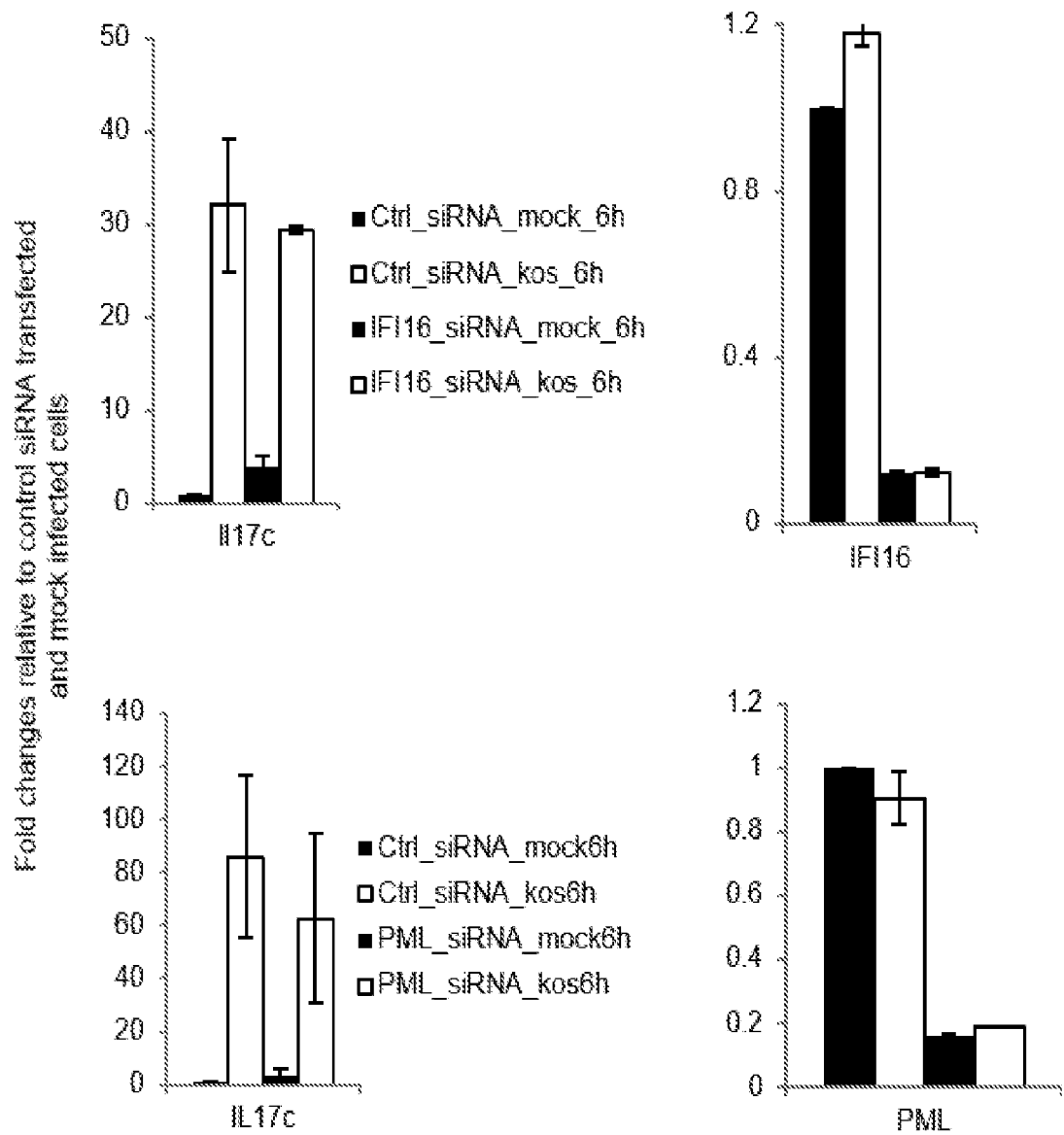

FIGS. 6A and 6B. siRNA knock-down of NFKB1, IRF1, IRF3 and IRF7 and similar expression of IL-17c in HSV infected primary human keratinocytes with reduced expression of IFI16 and PML. 6A. siRNA knock-down of gene expression of NF-κB, IRF1, IRF3 or IRF7 in primary keratinocytes. Primary keratinocytes were transfected with control siRNA or siRNA for NF-κB, IRF1, IRF3 or IRF7 for 48 hours and then mock infected or infected with KOS for 3 and 6 hours. Gene expression for NF-κB, IRF1, IRF3 and IRF7 were assayed by quantitative PCR. 6B. Expression of IL-17c in HSV infected keratinocytes with reduced expression of IFI16 and PML. Primary keratinocytes were transfected with control siRNA or siRNA for IFI16 or PML for 48 hours and then mock infected or infected with KOS for 6 hours.

Figure 7A:
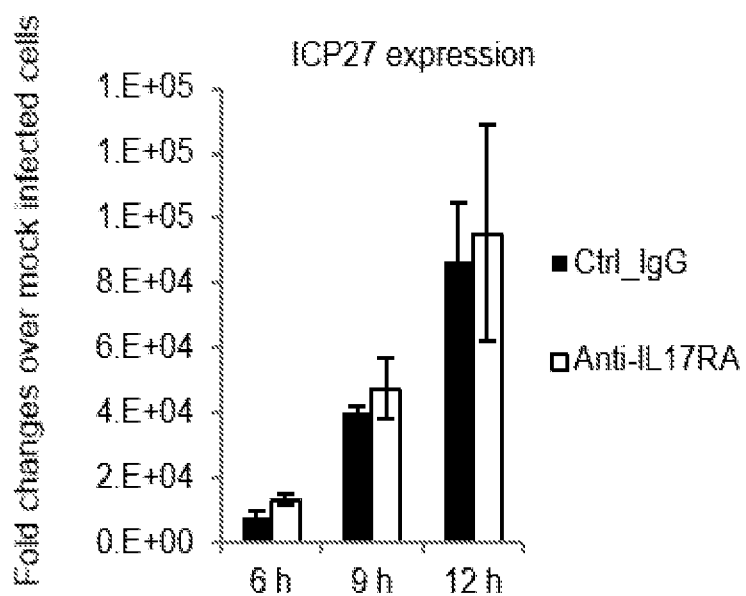
Figure 7B:
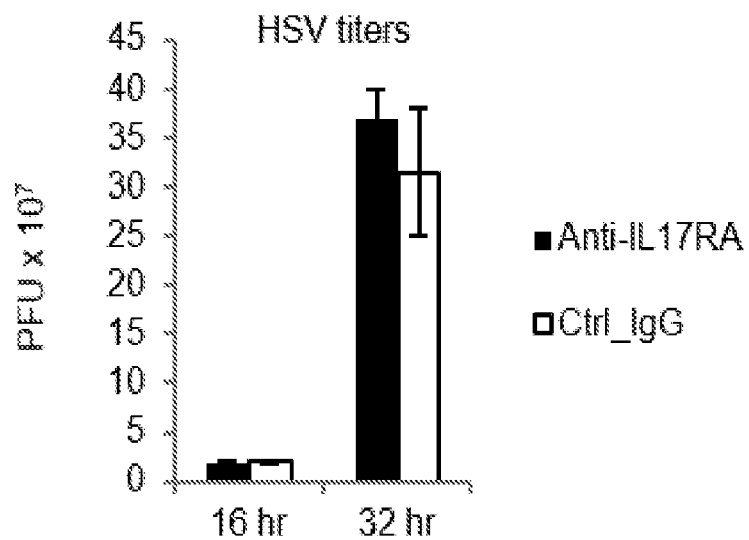
Figure 7C:
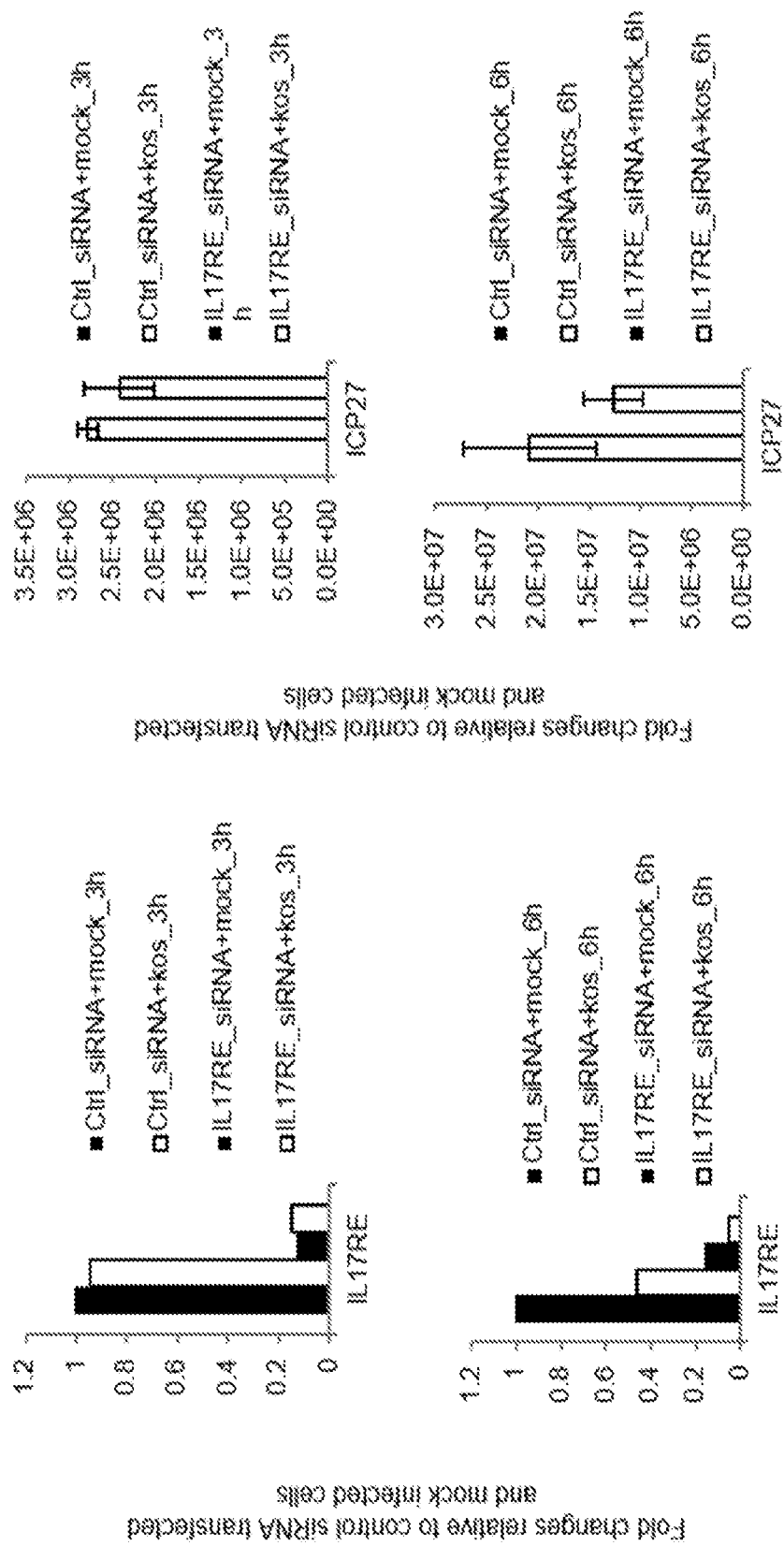
Figure 7C:
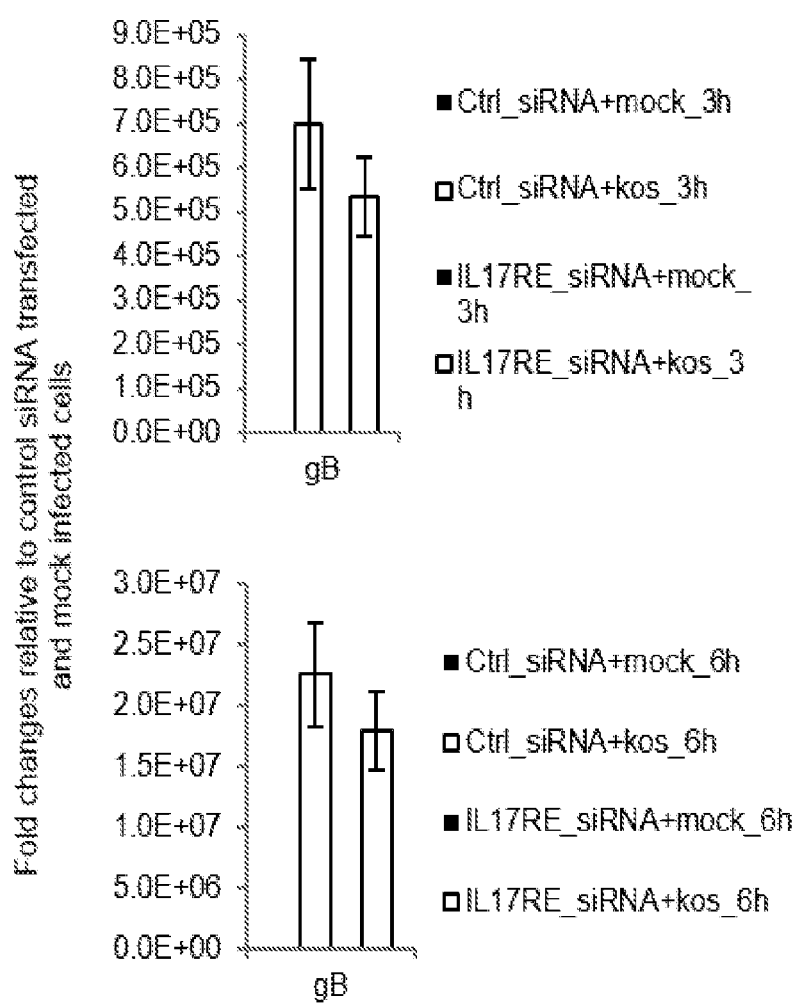

FIGS. 7A-7C. Blocking IL-17c signaling does not have significant effect on HSV gene expression or viral titers in infected human primary keratinocytes. Cells were untreated or pre-treated with an IL-17RA neutralizing antibody or matching control IgG for one hour before HSV-1 infection (7A & 7B). Gene expression of ICP27 was assayed by quantitative PCR and viral titers were determined by plaque assay in Vero cells. 7C. Primary keratinocytes were transfected with control siRNA or siRNA for IL-17RE for 48 hours and then mock infected or infected with KOS for 3 and 6 hours. Expression of ICP27, gB and IL-17RE was determined by quantitative PCR and viral titers were determined by plaque assay in Vero cells.

FIGS. 8A-8D. IL-17c stimulated neurite growth of differentiated SY5Y neurons. 8A. IL-17c induced directional neurite growth of differentiated SY5Y cells in a microfluidic device. SY5Y cells were differentiated with all trans retinoid acids (ATRA) at 20 µg/mL for 4 days and then placed in the wells on the left side of a microfluidic device with culture medium alone (M) or medium plus IL-17c or NGF on the other side. After 10 days of culture cells were fixed and stained with a PGP9.5 antibody. 8B-8D. IL-17c induced significantly more and longer neurites of differentiated SY5Y cells as compared to medium only or medium plus NGF. 8B. Comparison of growth cones of two neurites from medium only and medium plus IL-17c devices. 8C. The length of individual neurites that were extended into the main channel on the right side was measured in IMAGEJ. 8D. The error bar represents one standard deviation of data (number of neurites and total neurite length) from 3 microfluidic devices for each condition.

FIGS. 9A-9H. IL-17c induced neurite growth and branch points in HSN. HSN were isolated from individual human fetal spinal tissue and cultured in full neural medium only or medium plus IL-17c or NGF. 9A. Images of cultured HSN in the presence of IL-17c at 75 (top) and 90 (bottom) hours after plating. 9B. Live imaging of HSN to measure neurite length (left graph), neurite branch points (middle graph) and cell body area (right graph) every hour for 16 hours from hours 75 to 90 after HSN were plated in culture medium or medium plus IL-17c or NGF. 9C. Growth rates of neurite length (left graph), neurite branch points (middle graph) and cell body area (right graph) of cultured HSN from hours 75 to 90 after HSN were plated. 9D. A microfluidic device with three channels. HSN were placed in the middle channel and medium only (M) and medium plus IL-17c was placed on the left and right channels, respectively. DRG=dorsal root ganglia. 9E & 9F. HSN extended significantly longer neurites with more branch points into the channel with IL-17c containing medium. HSN were fixed and stained with PGP9.5 after 16 days of culture (9E) and number of neurites, total length and branch points were counted (9F). Scale bar=500 µm. 9G & 9H. The HSN neurites expressed IL-17RE. HSN in the three channel device were double stained with PGP9.5 and IL-17RE antibodies (9G). Comparison of growth cones of neurites from medium only and IL-17c containing channels (9H).

Figure 10A:
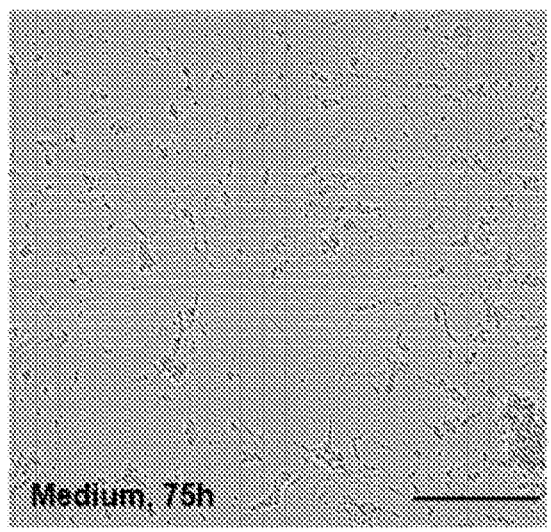
Figure 10A:
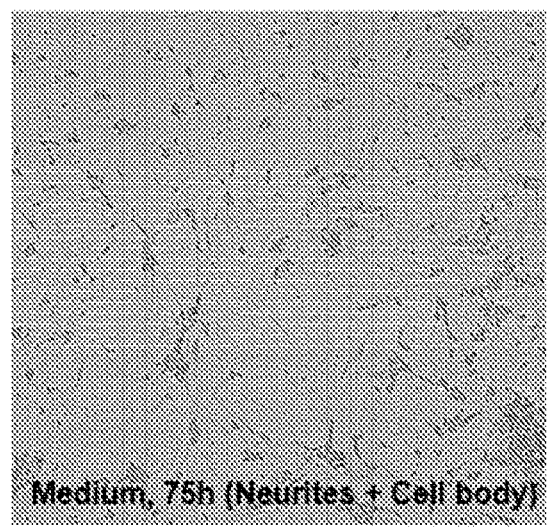
Figure 10A:
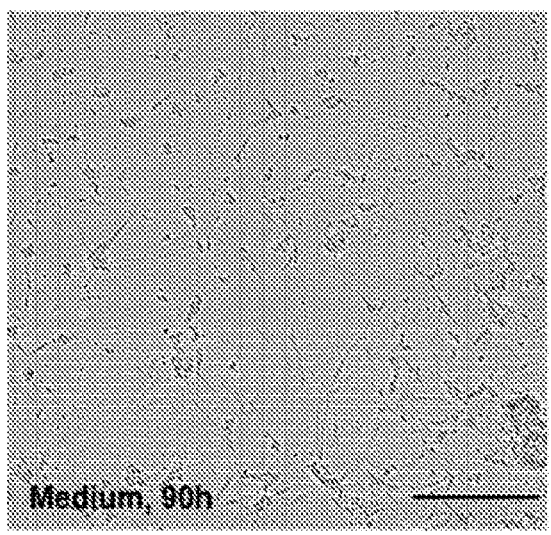
Figure 10A:
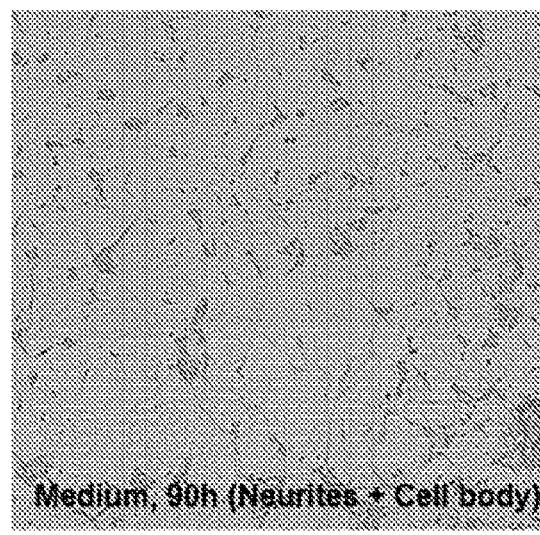
Figure 10B:
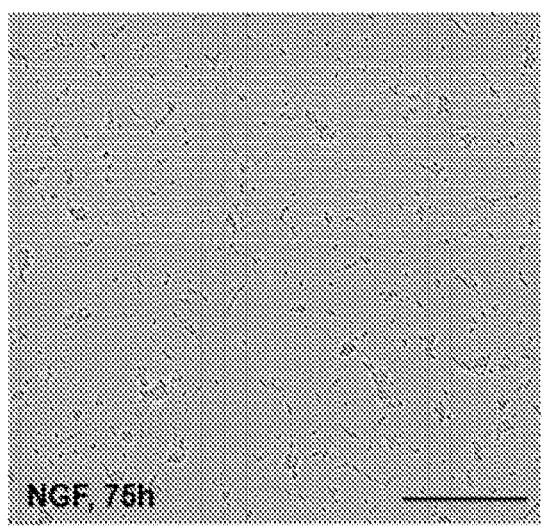
Figure 10B:
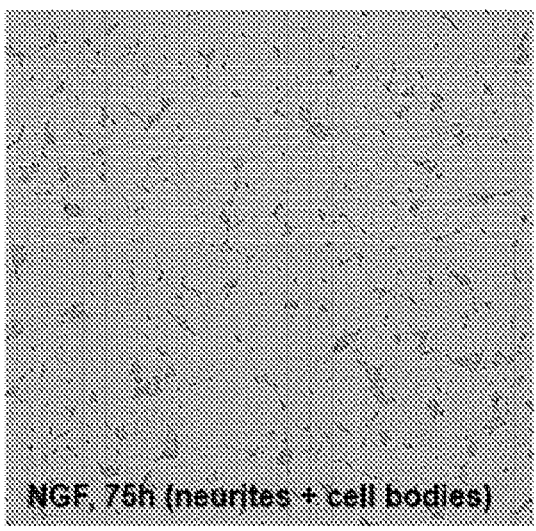
Figure 10B:
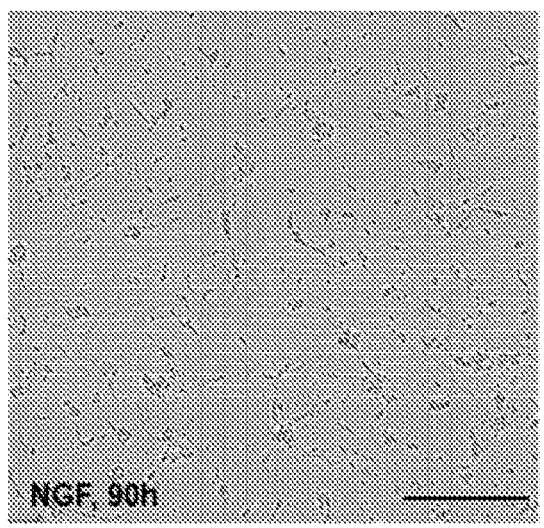
Figure 10B:
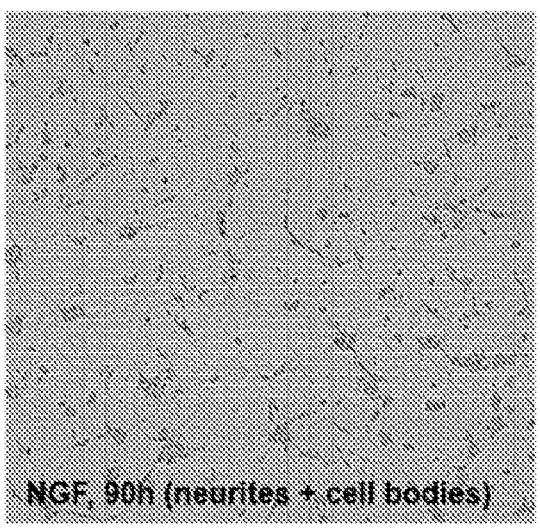
Figure 10C:
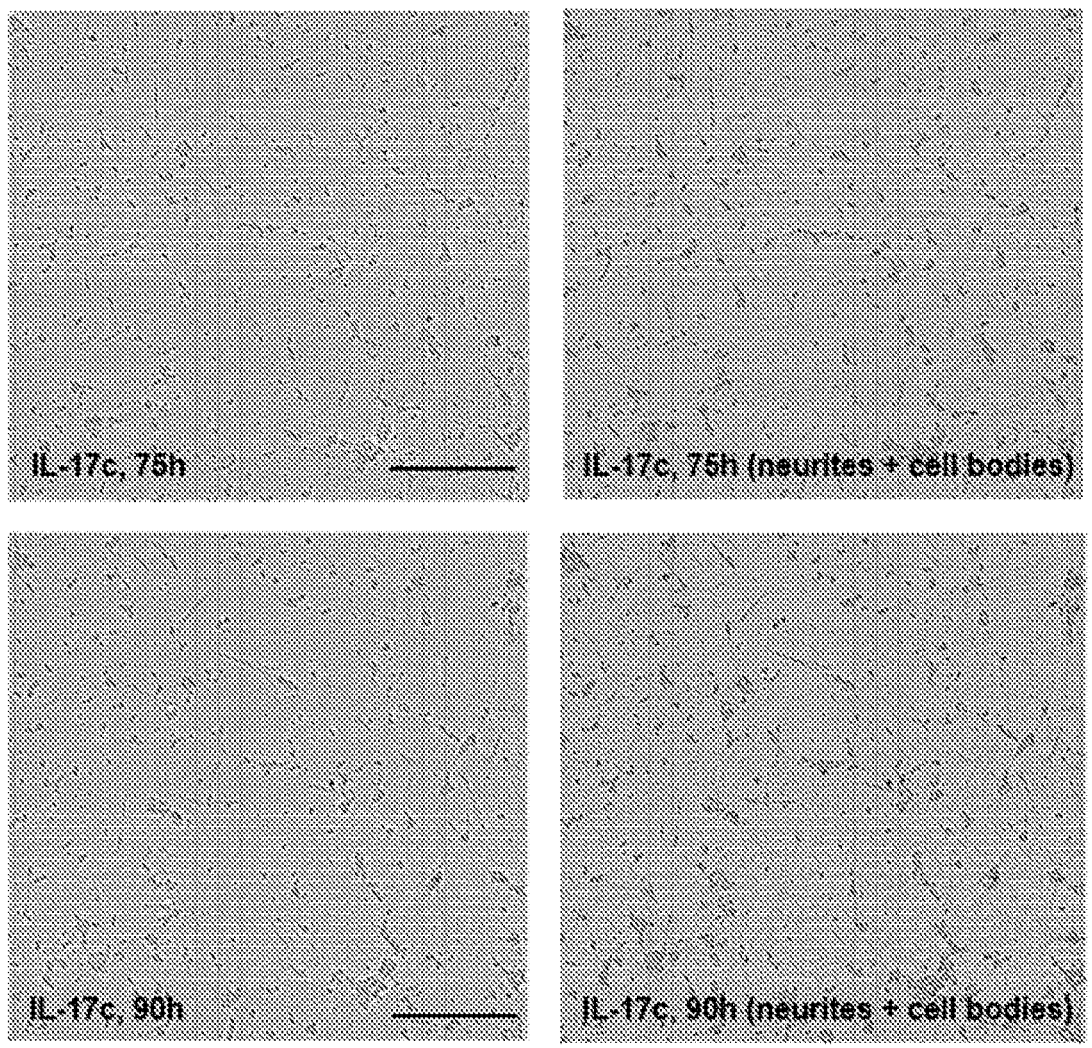

FIGS. 10A-10C. Bright field images of cultured human fetal sensory neurons (left) at 75 (top) and 90 hours (bottom); and cell body and neurite length and branch points were measured with the Incucyte neuro-track image analysis software module for both time points (right). FIG. 10A; medium. FIG. 10B; NGF. FIG. 10C; IL-17c.

FIGS. 11A-11D. IL-17c protects mouse primary cortical neurons and human primary keratinocytes from apoptosis during HSV infection. 11A. HSV infection induces expression of IL-17c and IL-17RE in MCN. Cells were infected with HSV-1 (K26) at MOI of 5 for 6, 12, 24 and 36 hours. Y-axis is fold change over mock infected MCN. Gene expression was determined by quantitative PCR. 11B. Detection by immunofluorescence of cleaved caspase 3 levels in K26 infected MCN. MCN were untreated or pre-treated with murine IL-17c (mIL17c) for 24 hours in the presence of a murine IL-17RA neutralizing antibody (anti-mIL17RA) or matching control rat IgG before K26 infection at MOI of 5 for 16 hours. Cells were stained with DAPI for cell nucleus and an antibody for cleaved caspase 3. K26 infected cells express GFP. 11C. Percentages of cleaved caspase 3+ neurons in K26 infected neurons pretreated with mIL-17c in the presence of anti-mIL17RA or control IgG. Error bars represent one standard deviation from the mean of three replicates. 11D. Exogenous human IL-17c (hIL17c) treatment provides a survival signal to keratinocytes (Kera) during HSV infection and a human IL-17RA neutralizing antibody (anti-hIL17RA) blocks its effect. Keratinocytes were untreated or pre-treated with hIL-17c for 12 hours in the presence of anti-hIL17RA or control IgG and then were mock or K26 infected (MOI of 2) for 12 hours.

Figure 12:
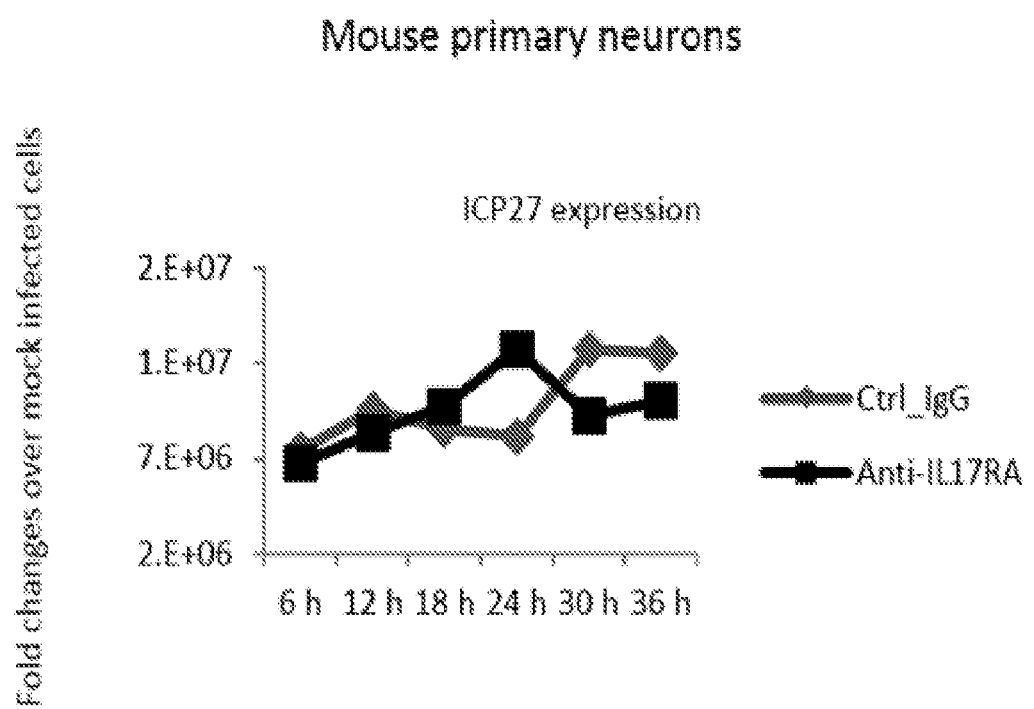

FIG. 12. Blocking IL-17c signaling does not have significant effect on HSV gene expression in infected mouse primary neurons. Cells were untreated or pre-treated with an IL-17RA neutralizing antibody or matching control IgG for one hour before HSV-1 Infection. ICP27 expression was determined by quantitative PCR.

DETAILED DESCRIPTION

There are a variety of conditions where neural growth and/or neural survival would be beneficial. For example, neurodegeneration is a damaged state of the nervous system evidenced by injured, diseased, or dysfunctional neural cells or nerves. Spinal cord injury and neurodegenerative disorders such as multiple sclerosis are examples of neurodegeneration. In the peripheral nervous system, neurodegeneration is referred to as neuropathy. Thus, neuropathies are a subtype of neurodegeneration. Neuropathies of the peripheral nervous system are estimated to affect 20 million people in the United States. Peripheral neuropathies often cause weakness, paralysis, numbness or pain (e.g., sensations of burning, stabbing pain, tingling and/or extreme sensitivity to touch). Approximately 30% of peripheral neuropathies are caused by diabetes; 30% are idiopathic; and other causes include autoimmune disorders, tumors, heredity, nutritional imbalances, infections, chemotherapy, medications, toxins, and accidents. Promotion of neural growth and/or neural survival would be beneficial in people and animals suffering from neurodegeneration.

Interleukins are a group of cytokines that function as part of the immune system. The Interleukin-17 family of cytokines is a group of pro-inflammatory cytokines secreted by activated memory T cells that play an active role in the inflammatory response. The Interleukin-17 family of cytokines has been implicated in inflammatory diseases and autoimmune diseases.

The present disclosure provides compositions, kits, and methods of promoting neural growth and/or neural survival using IL-17c. The compositions, kits, and methods can be used to promote neural growth and/or neural survival in a variety of conditions where such growth and survival is beneficial.

The Interleukin-17 cytokine family has six cytokines (Interleukins-17A through -17F); and there are five receptors (Interleukin-17RA through -17RE). IL-17 regulates the innate immune function of epithelial cells. Interleukin-17c (IL-17c) (SEQ ID NO. 1) is expressed in a wide variety of tissues. IL-17c is a 40 kDa protein having 197 amino acids, and 23% amino acid sequence identity to IL-17A. IL-17c binds to IL-17RE, a member of the IL-17 receptor family, and signals through a receptor heterodimeric complex formed by IL-17RA and IL-17RE. For more information regarding the interleukin-17 cytokine family, see, e.g., Krstic et al., Protein Pept Lett. 2015; 22(7):570-8; Shabgah et al., Postepy Dermatol Alergol. 2014 August; 31(4):256-61; Gaffen, Curr Opin Immunol. 2011 October; 23(5):613-9; Gaffen et al., Vitam Horm. 2006; 74:255-82; and Moseley et al., Cytokine Growth Factor Rev. 2003 April; 14(2):155-74.

IL-17c proteins include SEQ ID NO: 1 and biologically active analogues thereof. Biologically active analogues include proteins having at least 70% sequence identity with SEQ ID NO:1; at least 75% sequence identity with SEQ ID NO:1; at least 80% sequence identity with SEQ ID NO:1; at least 81% sequence identity with SEQ ID NO:1; at least 82% sequence identity with SEQ ID NO:1; at least 83% sequence identity with SEQ ID NO:1; at least 84% sequence identity with SEQ ID NO:1; at least 85% sequence identity with SEQ ID NO:1; at least 86% sequence identity with SEQ ID NO:1; at least 87% sequence identity with SEQ ID NO:1; at least 88% sequence identity with SEQ ID NO:1; at least 89% sequence identity with SEQ ID NO:1; at least 90% sequence identity with SEQ ID NO:1; at least 91% sequence identity with SEQ ID NO:1; at least 92% sequence identity with SEQ ID NO:1; at least 93% sequence identity with SEQ ID NO:1; at least 94% sequence identity with SEQ ID NO:1; at least 95% sequence identity with SEQ ID NO:1; at least 96% sequence identity with SEQ ID NO:1; at least 97% sequence identity with SEQ ID NO:1; at least 98% sequence identity with SEQ ID NO:1; or at least 99% sequence identity with SEQ ID NO:1; and the biologically active analogue also has at least 80%, 85%, 90%, 95%, 96%, 97%, 98%, 99%, 100%, 110%, 120%, 150%, 200%, 300%, 400%, 500%, 600%, 700%, 800%, 900%, 1000% or more of the biological activity of the IL-17c protein of SEQ ID NO:1.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" mean any set of values or parameters which originally load with the software when first initialized.

The biological activity of IL-17c and biologically active analogues thereof can be assessed using any relevant activity assay. In particular embodiments, activity can be assessed by treating human fetal sensory neurons with SEQ ID NO: 1 and/or biologically active analogues thereof. Neurite length, density, and/or branching points can be assessed within 3-4 days of treatment with IL-17c and/or biologically active analogues and/or other relevant control compounds.

Biologically active analogues of IL-17c can include variants, D-substituted analogs and modifications thereof.

"Variants" of proteins disclosed herein include proteins having one or more amino acid additions, deletions, stop positions, or substitutions, as compared to SEQ ID NO: 1.

An amino acid substitution can be a conservative or a non-conservative substitution. Variants of proteins disclosed herein can include those having one or more conservative amino acid substitutions. A "conservative substitution" involves a substitution found in one of the following conservative substitutions groups: Group 1: alanine (Ala or A), glycine (Gly or G), Ser, Thr; Group 2: aspartic acid (Asp or D), Glu; Group 3: asparagine (Asn or N), glutamine (Gln or Q); Group 4: Arg, lysine (Lys or K), histidine (His or H); Group 5: Ile, leucine (Leu or L), methionine (Met or M), valine (Val or V); and Group 6: Phe, Tyr, Trp.

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

"D-substituted analogs" include SEQ ID NO: 1 having one or more L-amino acids substituted with one or more D-amino acids. The D-amino acid can be the same amino acid type as that found in SEQ ID NO: 1 or can be a different amino acid. Accordingly, D-substituted analogs can also be variants.

Modified IL-17c (modifications) include SEQ ID NO: 1 changed to have a beneficial property such as (a) increased protein serum half-life and/or functional in vivo half-life, (b) reduced protein antigenicity, (c) increased protein storage stability, (d) increased protein solubility, (e) increased bioavailability (e.g. increased area under the curve (AUC)); (f) increased bioaccessibility to selected areas (e.g., to cross the blood brain barrier or to reach other physiologically protected areas); and/or (g) targeted delivery to reduce required dosage and/or avoid off-target side effects.

In particular embodiments, modified IL-17c proteins include IL-17c wherein one or more amino acids have been replaced with a non-amino acid component, or where the amino acid has been conjugated to a functional group or a functional group has been otherwise associated with an amino acid. The modified amino acid may be, for example, a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications also include nitrited IL-17c protein.

Regarding PEGylated amino acids, covalent attachment of proteins to PEG has proven to be a useful method to increase the circulating half-lives of proteins in the body (Abuchowski, A. et al., Cancer Biochem. Biophys., 1984, 7:175-186; Hershfield, M. S. et al., N. Engl. J. Medicine 316:589-596; and Meyers, F. J. et al., Clin. Pharmacol. Ther., 1991, 49:307-313). The attachment of PEG to proteins not only protects the molecules against enzymatic degradation, but also reduces their clearance rate from the body. The size of PEG attached to a protein has significant impact on the circulating half-life of the protein. The ability of PEGylation to decrease clearance is generally not a function of how many PEG groups are attached to the protein, but the overall molecular weight of the altered protein. PEGylation decreases the rate of clearance from the bloodstream by increasing the apparent molecular weight of the molecule. Up to a certain size, the rate of glomerular filtration of proteins is inversely proportional to the size of the protein. Usually the larger the PEG is, the longer the in vivo half-life of the attached protein is. In addition, PEGylation can also decrease protein aggregation (Suzuki et al., Biochem. Bioph. Acta vol. 788, pg. 248 (1984)), alter protein immunogenicity (Abuchowski et al.; J. Biol. Chem. vol. 252 pg. 3582 (1977)), and increase protein solubility as described, for example, in PCT Publication No. WO 92/16221. Several sizes of PEGs are commercially available (Nektar Advanced PEGylation Catalog 2005-2006; and NOF DDS Catalogue Ver 7.1). A variety of active PEGs have been used including mPEG succinimidyl succinate, mPEG succinimidyl carbonate, and PEG aldehydes, such as mPEG-propionaldehyde.

Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

While exemplary sequences are provided herein, sequence information provided by public databases can be used to identify related and relevant protein sequences and associated nucleic acid sequences encoding such proteins.

IL-17c (including biologically active analogues thereof) (individually and collectively, "active ingredients") can be provided alone or in combination within a composition. In particular embodiments, a composition includes at least one active ingredient and at least one pharmaceutically acceptable carrier. In addition or alternatively to administering an active ingredient directly as a therapeutic, compounds that stimulate IL-17c can also be administered. Such compounds include, for example, HSV (e.g., inactivated HSV) and toll-like receptor (TLR) ligands. These compounds, as well as their biologically active analogues, are also active ingredients within the scope of the disclosure.

Inactivated HSV is HSV in a non-infective (inactive) form. Examples of virus inactivation methods include solvent and/or detergent inactivation, pasteurization (e.g., heating to high temperatures), pH inactivation (e.g., using an acidic or alkaline pH; see, e.g., Lancz & Sample, Archives of Virology, March 1985, 84(1), 141-146 describing the thermal sensitivity of HSV at an alkaline pH), and irradiation (e.g., ultraviolet (UV) or gamma irradiation). HSV can be inactivated and safely administered to subjects. See, e.g., Whitley, Herpes Simplex Viruses, p. 2461-2509. In D. M. Knipe and P. M. Howley (ed.), Fields Virology, Fourth ed, vol. 2. Lippincott Williams & Wilkins, Philadelphia (2001).

Toll like receptors (TLRs) are a family of pattern recognition receptors that are activated by specific components of microbes and certain host molecules. They constitute the first line of defense against many pathogens and play a crucial role in the function of the innate immune system. It is estimated that most mammalian species have between ten and fifteen types of Toll-like receptors.

TLR ligands are widely available commercially, for example from Apotech and InvivoGen. Examples of TLR2 ligands include fungi, lipoglycans, lipopolysaccharides, lipoproteins, lipoteichoic acids, peptidoglycans, viral glycoproteins, and zymosan. More particular examples available from Invivogen include heat-killed: *Acholeplasma laidlawii* (*Mycoplasma*); *Escherichia coli; Helicobacter pylori; Listeria monocytogenes; Legionella pneumophila; Lactobacillus rhamnosus; Mycoplasma fermentans; Mycobacterium tuberculosis; Pseudomonas aeruginosa; Porphyromonas gingivalis; Staphylococcus aureus; Staphylococcus epidermidis; Streptococcus pneumonia*; and *Salmonella typhimurium*.

An example of a TLR5 ligand includes flagellin. More particular examples available from InvivoGen include flagellin from: *Bacillus subtilis; Pseudomonas aeruginosa*; and *Salmonella typhimurium*; including recombinant and mutant forms.

For additional information on TLRs and TLR ligands, see, Akira, Curr Opin Immunol 2003; 15(1): 5-11 and Akira and Hemmi, Immunol Lett 2003; 85(2): 85-95.

Salts and/or pro-drugs of active ingredients can also be used.

A pharmaceutically acceptable salt includes any salt that retains the activity of the active ingredient and is acceptable for pharmaceutical use. A pharmaceutically acceptable salt also refers to any salt which may form in vivo as a result of administration of an acid, another salt, or a prodrug which is converted into an acid or salt.

A prodrug includes an active ingredient which is converted to a therapeutically active compound after administration, such as by cleavage of a protein or by hydrolysis of a biologically labile group.

In some embodiments, the compositions include active ingredients of at least 0.1% weight/volume (w/v) or weight/weight (w/w) of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

Exemplary pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, release modifiers, salts, solvents or co-solvents, stabilizers, surfactants, and delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and trimethylamine salts.

An exemplary chelating agent is EDTA.

Exemplary isotonic agents include polyhydric sugar alcohols including trihydric and higher sugar alcohols, such as glycerin, erythritol, arabitol, xylitol, sorbitol, and mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl and propyl paraben, catechol, resorcinol, cyclohexanol, and 3-pentanol.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Del.), poly(vinyl alcohol) (PVA), Brij® (Croda Americas, Wilmington, Del.), sucrose acetate isobutyrate (SAIB), salts, and buffers.

Acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine, arginine and procaine.

Useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Stabilizers refer to a broad category of excipients which can range in function from a bulking agent to an additive which solubilizes the active ingredient or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars and sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on active ingredient weight.

The compositions disclosed herein can be formulated for administration by, for example, injection, inhalation, infusion, perfusion, lavage, ingestion, or absorption. The compositions disclosed herein can further be formulated for transdermal, intravenous, intradermal, intracranial, intracerebroventricular (ICV), intranasal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration. Compositions may be formulated for administration by sustained-release systems or by implantation devices. In certain embodiments, the compositions may be administered by bolus injection or continuously by infusion. Compositions may be administered by local administration or systemic administration.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, and alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated for topical administration. Topical administration refers to administration of a composition at the point of application. Topically applying describes application onto one or more surfaces including epithelial surfaces. A substance delivered by topical administration may not reside in the skin for an extended period of time, but instead may penetrate into localized tissue, deep tissue and/or synovial fluids in order to have an effect on localized tissue, deep tissue, or joints, or any combination thereof.

Compositions can be formulated for transdermal delivery. Transdermal delivery refers to the delivery of a compound, for example, an active ingredient of this disclosure or other therapeutic agent, through one or more layers of the skin (e.g., epidermis and dermis). Transdermal delivery may include administration of the composition to the skin surface of a subject so that the active ingredient passes through the skin tissue and into deeper tissue thereby providing effects in deep tissue. In some embodiments, transdermal delivery systems include use of a patch, iontophoresis, or magnetophoresis, or any combination thereof. In some embodiments, transdermal delivery is enhanced, wherein enhancement may be through chemical or physical means.

A patch refers to a medicated patch, e.g., a patch with a composition including at least one active ingredient that is placed on the skin to deliver a dosage of the active ingredient through the skin and into the surrounding tissue. In some embodiments, the active ingredient may penetrate deeply below the skin to a site for deep tissue effects. In some embodiments, the active ingredient penetrates just below the skin to a localized site for a local effect. In some embodiments, the dosage of the active ingredient provides minimal entry of the active ingredient into the blood stream. In other embodiments, the dosage provides no entry of the active ingredient into the blood stream.

Transdermal patches are a well-accepted technology used to deliver a wide variety of active ingredients. Patches may be placed on the skin for specified therapeutic time periods. Patches may include an adhesive to remain in place when placed on the skin or may be adhered by other means including adhesive tape or strips. In addition, patches may be perforated or stretchable in order that they may be wrapped around an appendage or body part. In certain embodiments, a stretchable patch may be wrapped fully around an appendage or body part. In alternative embodiments, a stretchable patch may be wrapped partly around an appendage or body part. For example, a patch may be wrapped around a knee, ankle, leg, elbow, wrist, finger, arm, or neck.

Conventional dermal patches include a carrier that holds an active ingredient and allows the active ingredient to be released onto a subject's skin for absorption. Many different kinds of dermal patches are known, including matrix-type patches, reservoir-type patches, multi-laminate drug-in-adhesive type patches, monolithic drug-in-adhesive type patches, and many others. Such patches can be readily prepared using technology which is known in the art such as described in Remington's Pharmaceutical Sciences, 18th or 19th editions, published by the Mack Publishing Company of Easton, Pa. and "Transdermal And Topical Drug Delivery Systems" (Tapash K. Ghosh et al. eds., 1997); see also Kristine Knutson and Lynn K. Pershing, Topical Drugs, in Remington: The Science And Practice Of Pharmacy 866-885 (Alfonso R. Gennaro ed., 1995).

A penetration enhancer may be used with the compositions. Penetration enhancers refer to agents known to accelerate the delivery of an active ingredient through the skin. Suitable penetration enhancers include dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols including menthol, and the like. The permeation enhancer may also be a vegetable oil. Such oils include safflower oil, cottonseed oil and corn oil. Additional penetration enhancers may generally be found in Remington's Pharmaceutical Sciences, 18th or 19th editions, published by the Mack Publishing Company of Easton, Pa. In certain embodiments, the permeation enhancer is a component of the composition. In one embodiment, a patch includes a permeation enhancer in an amount effective to enhance promotion of neural growth and/or neural survival by an active ingredient. In some embodiments physical permeation enhancer techniques may be used including magnetophoresis, iontophoresis or a battery-powered electronic stimulant.

Iontophoresis can be used for transdermal active ingredient delivery. Iontophoresis, also known as Electromotive Drug Administration (EMDA), is a technique using a small electric charge to deliver an active ingredient or other chemical through the skin. It may function similar to an injection without the needle, for example EMDA may be used for localized entry of an active ingredient into the skin. In addition, EMDA may be used for concentrated application of an active ingredient under the skin.

Magnetophoresis refers to the motion of dispersed magnetic particles relative to a fluid under the influence of a magnetic field. Magnetophoresis may provide enhancing delivery across biological barriers, including intact skin. In some embodiments, iontophoresis or magnetophoresis may be used as a transdermal delivery system alone or in combination with other forms of administration.

Microneedle technology may be used. Microneedle transdermal delivery systems include microneedle patches as well as microneedle systems that can accommodate transdermal delivery of larger volumes of active ingredient. Microneedles may be solid or hollow, and allow for delivery of small molecule, large molecule and biologically active ingredients. Microneedle devices are well-suited for dermal skin targets, and are available in a variety of lengths, depending on the desired depth of the delivery. Hollow microneedles are available in a variety of sizes to accommodate various volumes of active ingredient. Dissolving microneedle patches may be also be used.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days. Depot preparations can be administered by injection; parenteral injection; instillation; or implantation, for example, into soft tissues, a body cavity, or occasionally into a blood vessel with injection through fine needles.

Depot formulations can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Compositions may be formulated for administration locally via implantation of a membrane, sponge or another appropriate material onto which the active ingredient has been absorbed or encapsulated. In certain embodiments, where an implantation device is used, the device may be implanted into any suitable tissue or organ, and delivery of the desired active ingredient may be via diffusion, timed-release bolus, or continuous administration. Examples include chitosan sponges and collagen sponges.

In particular embodiments, active ingredients are administered by a heparin-based delivery system (HBDS), an affinity-based delivery system that regulates the slow release of active ingredients by binding them to heparin in fibrin gels. An HBDS typically contains three main components: (1) a synthetic linker peptide, (2) the polysulfated glycosaminoglycan heparin, and (3) the active ingredient(s) to be delivered. Administration of the compositions may also be achieved by locally supplying active ingredients using poly(ethylene-co-vinyl acetate) (EVAc) matrices.

In particular embodiments, compositions can be formulated with molecular linkages that facilitate delivery to the central nervous system (e.g., brain and spinal cord). Particular embodiments targeting the central nervous system can utilize agents that bind the transferrin receptor. One example is OX26, a peptidomimetic MAb that undergoes receptor mediated transcytosis following binding to the transferrin receptor. See also, e.g., U.S. Pat. No. 6,372,250B1.

Nanocarriers can protect therapeutics from degradation during transport to an active site, and can also aid in transport across the blood-brain-barrier. Examples of nanocarriers include liposomes, polymeric nanoparticles, and solid lipid nanoparticles. Therapeutics can be covalently linked to nanocarriers, or can be encapsulated without linkages.

Compositions can be formulated for intranasal delivery. Intranasal delivery refers to the delivery of a compound to the nasal passages. When a nasal drug formulation is delivered deep and high enough into the nasal cavity, the olfactory mucosa can be reached and drug transport into the central nervous system via the olfactory receptor neurons can occur. Intranasal administration can rapidly achieve therapeutic central nervous system concentrations by delivering therapeutics across the blood-brain-barrier. Intranasal delivery across the blood-brain-barrier can be achieved using a propellant device. See for example, US Patent Application Publication No. 2014/0014104.

Compositions may be formulated for administration by, or used in combination with, means of guiding neurite growth, for example, axonal regrowth to facilitate nerve growth. The neurite guidance may be used to bridge gaps between nerve endings. One example is nerve guidance conduits, also referred to as entubulation, which are composed of biological or synthetic materials and facilitate communication between proximal and distal ends of a nerve gap, block external inhibitory factors, and act as physical axon guidance. In some embodiments, polymer-based active ingredient delivery may be used with nerve guidance conduits. Compositions may also be used with longitudinally-oriented channels, macroscopic structures that can be added to a conduit as a scaffold. Scaffolds may use materials such as chitosan or collagen.

The compositions, kits, and methods may also use vector-mediated gene delivery techniques to direct expression of active ingredients. A cell line expressing one or more active ingredients may be established within the subject or transplanted to the area of interest, thereby delivering active ingredient to the affected area. Such a cell line may be a cell line that endogenously expresses an active ingredient (e.g., IL-17c); may be a transgenic cell line expressing an active ingredient; or established by transfection and selection using a vector encoding an active ingredient. Viral vector-mediated gene delivery may also be used whereby a viral vector encoding an active ingredient is delivered directly to the cells of a subject in the area of interest.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, compositions can be prepared to meet sterility, pyrogenicity, general safety, and purity standards as required by U.S. FDA Office of Biological Standards and/or other relevant foreign regulatory agencies.

Methods of Use. Methods disclosed herein include treating subjects (humans, veterinary animals, dogs, cats, reptiles, birds, etc.), livestock (horses, cattle, goats, pigs, chickens, etc.), and research animals (monkeys, rats, mice, fish, etc.) with active ingredients disclosed herein including salts and prodrugs thereof. Treating subjects includes delivering therapeutically effective amounts. Therapeutically effective amounts include those that provide effective amounts, prophylactic treatments, and/or therapeutic treatments.

An "effective amount" is the amount of an active ingredient or composition necessary to result in a desired physiological change in a subject. Effective amounts are often administered for research purposes. Effective amounts disclosed herein promote neural growth and/or neural survival in an animal or clinical research model of a condition where promotion of neural growth and/or neural survival is beneficial. For example, exemplary animal models for diabetic neuropathy include: a streptozotocin (STZ)-induced diabetes mellitus model in a normal genetic background in rats; non-obese diabetic (NOD) mice; Bio-Breeding/Worcester (BB/W) rat; and the Zucker diabetic, genetically obese rat. Other animal models for diabetes can be found in Sullivan K A, Lentz S I, Roberts J L, Jr, Feldman E L. "Criteria for creating and assessing mouse models of diabetic neuropathy." Current Drug Targets. 2008; 9:3-13. doi: 10.2174/138945008783431763.

Exemplary animal models for chemical neuropathy use chemotherapeutic regimens including: taxanes (e.g. docetaxel or paclitaxel); platinum compounds (e.g. cisplatin, carboplatin, and oxaliplatin); and others such as vincristine, thalidomide, suramin, and bortezomib. Chemotherapies can be injected intravenously or intraperitoneally.

Exemplary animal models for HIV-associated sensory neuropathies (HIV-SN) include a transgenic mouse model, where gp120 (the HIV envelope protein) is expressed under the GFAP promoter. Treatment of the transgenic mouse with didanosine further accelerates developing neuropathy and results in degeneration of distal axons of unmyelinated fibers. Injection of toxic anti-retroviral drugs, such as didanosine or stavudine, into mice has been used to study neuropathic pain.

Exemplary animal models for multiple sclerosis include experimental autoimmune encephalomyelitis (EAE), a family of disease models, used as the most widely applied means of studying MS; virus-induced demyelinating disease; toxin induced models of demyelination (e.g. copper chelator cuprizone); and toxin induced models of oligodendrocyte death (e.g. diphtheria toxin A). Exemplary models of spinal cord injury include contusion, compression and transection models.

Assays to determine outcome measures in neurodegeneration animal models include electrophysiological measurements such as nerve action potentials, and conduction velocity. Skin biopsies, such as punch biopsies, at various sites are used to evaluate peripheral neuropathies and can be combined with markers such as pan-axonal marker, pgp9.5. Intraepidermal nerve fiber density may also be used, for example, as a true morphological correlate of the degree of sensory axon loss. Mitochondrial abnormalities may also be assessed to determine axonal degeneration.

Behavioral tests that may be used to assess neurodegeneration include locomotor tests (testing the locomotor apparatus of the animal); motor tests (analyzing the strength, coordination and other abilities of the skeletal muscles); sensory tests (evaluating proprioception, touch, pain or temperature sensing); sensory-motor tests; (testing the proper connection between the sensory and motor systems); autonomic tests; (evaluating the function of the sympathetic and parasympathetic systems); and reflex response based tests. Sensory behavioral testing includes evaluating sensations such as thermal hyperalgesia by the tail flick test and the hot plate method; mechanical hyperalgesia; mechanical allodynia; and chemical allodynia.

A "prophylactic treatment" includes a treatment administered to a subject who does not display signs or symptoms of neurodegeneration; or only displays early signs or symptoms of neurodegeneration such that treatment is administered for the purpose of promoting neural growth and/or neural survival for the purpose of diminishing, preventing, or decreasing the risk of developing neurodegeneration further. Thus, a prophylactic treatment functions as a preventative treatment against neurodegeneration.

A "therapeutic treatment" includes a treatment administered to a subject who displays symptoms or signs of neurodegeneration, and is administered to the subject for the purpose of promoting neural growth and/or neural survival to alleviate symptoms associated with the neurodegeneration.

Symptoms of neurodegeneration can include disruptions or conditions of the somatosensory system, including disruptions of nociception, mechanoreception, proprioception, and thermoreception. Symptoms of neurodegeneration can also include hyperesthesia (an abnormal increase in sensitivity to a sensory stimulus, such as the sensation of pain in response to a stimulus that is normally not painful), hypoesthesia (reduced sensation, or a partial loss of sensitivity to sensory stimuli), anesthesia (a lack of sensation) paresthesia (abnormal sensation, including the sensations of tingling, tickling, pricking, burning, or stabbing pain without corresponding sensory stimulus), hyperalgesia (increased sensitivity to pain), and allodynia (sensation of pain due to a non-noxious stimulus). These sensory disturbances may be characterized further by their location, pattern of onset, consistency, and factors that exacerbate or alleviate symptoms.

Symptoms of neurodegeneration also can include neuropathic pain, often the result of peripheral neuropathies. Neuropathic pain refers to pain that originates from pathology of the nervous system. Neuropathic pain may result from lesions of the nervous system.ABnormal signals arise not only from injured axons but also from the intact nociceptors that share the innervation territory of an injured nerve. The nervous system can generate and perpetuate pain without any ongoing stimuli from injury. Neuropathic pain is often puzzling and frustrating for both patients and physicians because it seems to have no cause; responds poorly to standard pain therapies; can last indefinitely and even escalate over time; and often results in severe disability.

Additional symptoms of neurodegeneration can be paralysis, difficulty of movement, speech impairment, tremors, and cognitive impairment. Causes of neurodegeneration in the central nervous system include spinal cord injury and multiple sclerosis, for example.

Additional exemplary degenerative nerve diseases or conditions leading to neurodegeneration include Alzheimer's disease; amyotrophic lateral sclerosis; Friedreich's ataxia; Huntington's disease; Lewy body disease; Parkinson's disease; and spinal muscular atrophy. Exemplary motor neuron diseases or conditions leading to neurodegeneration include amyotrophic lateral sclerosis (ALS), also called Lou Gehrig's disease; progressive bulbar palsy; pseudobulbar palsy; primary lateral sclerosis (PLS); progressive muscular atrophy; spinal muscular atrophy (SMA); and post-polio syndrome (PPS).

Neurodegeneration can be idiopathic. Neurodegeneration can also be small fiber neuropathies. Neurodegeneration can be caused by alcoholism; bone marrow disorders (e.g., abnormal monoclonal gammopathies, amyloidosis, osteosclerotic myeloma, lymphoma); diseases (e.g., autoimmune diseases (e.g., chronic inflammatory demyelinating polyneuropathy, Guillain-Barre syndrome, lupus, multiple sclerosis, spinal cord injury, necrotizing vasculitis, rheumatoid arthritis, Sjogren's syndrome); connective tissue disorders; diabetes mellitus; hypothyroidism; kidney disease; liver disease; exposure to poisons or toxins (e.g., heavy metals or chemicals); infections (e.g., viral or bacterial including Lyme disease, shingles (i.e. varicella-zoster), Epstein-Barr virus, hepatitis C, herpes, leprosy, diphtheria and human immunodeficiency virus (HIV)); injuries (e.g., from nerve pressure (from, e.g., cancerous and noncancerous growths on the nerves themselves, or in an area that puts pressure on surrounding nerves), repetitive motion or trauma); inherited causes or disorders (e.g., Charcot-Marie-Tooth disease); medical conditions; medical treatments (e.g., chemotherapy or radiation therapy); medications; metabolic problems; and vitamin deficiencies (e.g., vitamin B-1, B-3, B-6, B-12, E).

Therapeutically effective amounts generating promotion of neural growth and/or neural survival can be evidenced by increased neurite growth (e.g., axon and/or dendrite growth), neurite guidance in a particular direction, increased branching points of neurites or nerve fibers, increased innervation, neural cell survival, neural cell regeneration, nerve cell or nerve fiber density, nerve fiber growth, nerve fiber length, or decreased apoptosis, degeneration of cells, neurite degeneration, or neural cell degeneration.

Subjects also may be assessed for promotion of neural growth and/or neural survival by a number of accepted procedures known in the art including electrodiagnostic tests such as Nerve Conduction Studies and Electromyography (EMG); and Nerve Conduction Velocity tests that evaluate how nerves transmit electrical stimuli by measuring the speed of conduction of an electrical impulse. These tests can help determine whether neurodegeneration involves axons or myelin. EMG measures the electrical activity of muscles in response to nerve stimulations. Skin Biopsy may also be used to measure nerve fibers in the skin and to identify specific neuropathies, such as small fiber neuropathy. In particular, skin punch biopsy may be used at standard sites to measure the density of the small nerve fibers, as determined by morphometry after immunostaining, for example, with an antibody to the axonal marker pgp 9.5.

Autonomic Tests also may be used to assess neural growth and/or neural survival, including the Quantitative Sudomotor Axon Reflex Test (QSART) and the tilt table test. QSART measures the autonomic nerve fibers that stimulate sweating. The tilt table test measures changes in blood pressure and pulse from prone to vertical positions.

Tests used to assess neural growth and/or neural survival related to neurodegeneration include symptoms, signs or evidence indicating disease of the brain or spinal cord. Evidence of two or more lesions, or abnormal areas in the brain, using a Magnetic Resonance Imaging (MRI) scan may be identified. Evoked potential tests may be performed to measure the time it takes to respond to stimulation (i.e. visual, auditory and somatosensory). Tests for infection, for example, in cerebrospinal fluid may also be administered. Spinal cord injury may be identified by computerized tomography (CT) scan; x-ray; and MRI.

Therapeutically effective amounts generating promotion of neural growth and/or neural survival also can be evidenced by reduction in a symptom associated with neurodegeneration.

In various embodiments, the compositions, kits, and methods are used to promote neural growth and/or neural survival in the autonomic nervous system, the central nervous system, the parasympathetic nervous system, the peripheral nervous system, the sensory nervous system, and/or the sympathetic nervous system.

In various embodiments, the compositions, kits, and methods are used to promote neural growth and/or neural survival of neural progenitor cells, autonomic nerve fibers, motor nerve fibers, motor neurons, proprioceptive sensory fibers, sensory nerve fibers, and/or sensory neurons.

In particular embodiments, the compositions, kits, and methods may be used in the dermis, epidermis or at the dermal-epidermal junction.

Administering in or around a site of means within 5 inches of a site of interest; within 4 inches of a site of interest; within 3 inches of a site of interest; within 2 inches of a site of interest; or within 1 inch of a site of interest.

In various embodiments, the compositions, kits, and methods may be used in combination with other treatments including treatment of the underlying cause of the neurodegeneration, such as a vitamin deficiency, an infection, a neurodegenerative disorder (e.g., Alzheimer's disease, Parkinson's disease), or a procedure or treatment such as surgery or chemotherapy. In particular embodiments, they may be used in combination with surgical removal of a tumor that put pressure on surrounding nerves.

A subject in need of promotion of neural growth and/or neural survival can be a subject that has been assessed for neurodegeneration and found to have a symptom of the neurodegeneration or has been determined to be at risk for developing neurodegeneration. Methods for assessing subjects for neurodegeneration include any art-accepted test including the exemplary art-accepted tests disclosed herein. For example, a subject may be assessed for symptoms including sensory disturbances by positive features (too much sensation, spontaneous sensation, etc.), or negative sensory deficits (too little sensation or numbness). A subject in need of promotion of neural growth and/or neural survival can also be a research animal undergoing experimental procedures in an animal model of neurodegeneration (e.g., spinal cord injury or diabetic neuropathy).

Assessment of a subject for neurodegeneration can include evaluation of a subject's medical history using information that may include past medical conditions; family history; symptom onset; progression and pattern of involvement; co-existing medical conditions; previous treatments; and medications. Assessment may also involve a neurological examination to evaluate motor and sensory nerve functions; strength and sensation; balance; coordination; and reflexes, as well as evaluation of biomarkers of nerve presence and function (e.g., MRI, PET, and radionucleotide imaging).

The actual dose amount administered to a particular subject can be determined by a physician, veterinarian, or researcher taking into account parameters such as physical and physiological factors including target area; body weight; severity of neurodegeneration or resulting condition; prospective conditions; type of neural cells or neurites requiring growth and/or survival promotion; previous or concurrent therapeutic interventions; idiopathy of the subject; and route of administration.

The amount and concentration of an active ingredient(s) in a composition, as well as the quantity of the composition administered to a subject, can be selected based on clinically relevant factors, the solubility of the active ingredient in the composition, the potency and activity of the active ingredient, and the manner of administration of the composition, as well as whether the active ingredient is modified (e.g., nitrited, PEGylated) or administered in combination with other treatments.

A composition including a therapeutically effective amount of an active ingredient(s) disclosed herein can be administered to a subject for promoting neural growth and/or neural survival in a clinically safe and effective manner, including one or more separate administrations of the composition.

Useful doses can often range from 0.1 to 5 µg/kg. Other doses can range from 1-2 mg/kg, 1-5 mg/kg, 1-10 mg/kg, 1-15 mg/kg, 1-25 mg/kg, 1-50 mg/kg, 1-55 mg/kg, 1-100 mg/kg, 1-250 mg/kg, 1-500 mg/kg, 1-750 mg/kg, or 1-1000 mg/kg. In other examples, a dose can include 1 µg/kg, 10 µg/kg, 50 µg/kg, 75 µg/kg, 100 µg/kg, 150 µg/kg, 200 µg/kg, 500 µg/kg, 1000 µg/kg, 0.1 to 5 mg/kg, or from 0.5 to 1 mg/kg. In other examples, a dose can include 1 mg/kg, 10 mg/kg, 25 mg/kg, 50 mg/kg, 55 mg/kg, 100 mg/kg, 250 mg/kg, 500 mg/kg, 750 mg/kg, 1000 mg/kg, or more.

Each of the described doses of active ingredients can be an active ingredient alone, or in combination of one or more other active ingredients. In particular embodiments, when included in combinations to produce a dose, such as a dose stated herein, the substituents in the combination can be provided in exemplary ratios such as: 1:1; 1:1.25; 1:1.5; 1:1.75; 1:8; 1:1.2; 1:1.25; 1:1.3; 1:1.35; 1:1.4; 1:1.5; 1:1.75; 1:2; 1:3; 1:4; 1:5; 1:6:1:7; 1:8; 1:9; 1:10; 1:15; 1:20; 1:30; 1:40; 1:50; 1:60; 1:70; 1:80; 1:90; 1:100; 1:200; 1:300; 1:400; 1:500; 1:600; 1:700; 1:800; 1:900; 1:1000; 1:1:1; 1:2:1; 1:3:1; 1:4:1; 1:5;1; 1:10:1; 1:2:2; 1:2:3; 1:3:4; 1:4:2; 1:5:3; 1:10:20; 1:2:1:2; 1:4:1:3; 1:100:1:1000; 1:25:30:10; 1:4:16:3; 1:1000:5:15; 1:2:3:10; 1:5:15:45; 1:50:90:135; 1:1.5:1.8:2.3; 1:10:100:1000 or additional beneficial ratios depending on the number and identity of substituents in a combination to reach the stated dosage. The substituents in a combination can be provided within the same composition or within different compositions.

Therapeutically effective amounts can be achieved by administering single or multiple doses during the course of a treatment regimen (e.g., QID, TID, BID, daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

Compositions may be administered before an upcoming insult, such as administration of chemotherapy, radiation, or medications that may cause neurodegeneration. In particular embodiments, compositions are administered within 10 days of an upcoming insult, within 9 days of an upcoming insult, within 8 days of an upcoming insult, within 7 days of an upcoming insult, within 6 days of an upcoming insult, within 5 days of an upcoming insult, within 4 days of an upcoming insult, within 3 days of an upcoming insult, within 48 hours of an upcoming insult, within 46 hours of an upcoming insult, within 44 hours of an upcoming insult, within 42 hours of an upcoming insult, within 40 hours of an upcoming insult, within 38 hours of an upcoming insult, within 36 hours of an upcoming insult, within 34 hours of an upcoming insult, within 32 hours of an upcoming insult, within 30 hours of an upcoming insult, within 28 hours of an upcoming insult, within 26 hours of an upcoming insult, within 24 hours of an upcoming insult, within 22 hours of an upcoming insult, within 20 hours of an upcoming insult, within 18 hours of an upcoming insult, within 16 hours of an upcoming insult, within 14 hours of an upcoming insult, within 12 hours of an upcoming insult, within 10 hours of an upcoming insult, within 8 hours of an upcoming insult, within 6 hours of an upcoming insult, within 4 hours of an upcoming insult, or within 2 hours of an upcoming insult. In one particular embodiment, compositions are administered within 18 hours of an upcoming insult.

Also disclosed herein are kits including one or more containers including one or more of the active ingredients and/or compositions described herein. In various embodiments, the kits may include one or more containers containing one or more active ingredients and/or compositions to be used in combination with the active ingredients and/or compositions described herein. Associated with such container(s) can be a notice in the form prescribed by a governmental agency regulating the manufacture, use, or sale of pharmaceuticals or biological products, which notice reflects approval by the agency of manufacture, use, or sale for human administration.

Optionally, the kits described herein further include instructions for using the kit in the methods disclosed herein. In various embodiments, the kit may include instructions regarding preparation of the active ingredients and/or compositions for administration; administration of the active ingredients and/or compositions; appropriate reference levels to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. The instructions may be in English and/or in any national or regional language. In various embodiments, possible side effects and contraindications to further use of components of the kit based on a subject's symptoms can be included. The kits and instructions can also be tailored according to the area of the body to be treated.

In various embodiments, the packaging, active ingredients and/or compositions, and instructions are combined into a small, compact kit with printed instructions for use of each of the active ingredients and/or compositions. In various embodiments in which more than one active ingredient and/or composition is provided, the sequencing of use of the active ingredients and/or compositions can be labeled in the kit.

In various embodiments, the kits described herein include some or all of the necessary medical supplies needed to use the kit effectively, thereby eliminating the need to locate and gather such medical supplies. Such medical supplies can include syringes, ampules, tubing, facemask, a needleless fluid transfer device, an injection cap, sponges, sterile adhesive strips, Chloraprep, gloves, and the like. Variations in contents of any of the kits described herein can be made.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A method of promoting neural growth and/or neural survival in a subject including administering to the subject a therapeutically effective amount of an IL-17c protein thereby promoting neural growth and/or neural survival in the subject
2. A method of embodiment 1, wherein the neural growth is evidenced by nerve density, neurite growth (axon or dendrite) and/or neurite (axon or dendrite) guidance.
3. A method of embodiments 1 or 2, wherein the IL-17c protein includes SEQ ID NO: 1.
4. A method of any of embodiments 1-3, wherein the promoted neural growth and/or neural survival is found in a sensory or motor neural cell and/or nerve.
5. A method of any of embodiments 1-4, wherein the administering is in or around a site of the sensory or motor neural cell and/or nerve.
6. A method of any of embodiments 1-5, wherein the administering is topical.
7. A method of any of embodiments 1-6, wherein the administering is through application of a transdermal patch.
8. A method of any of embodiments 1-7, wherein the administering is prophylactic.
9. A method of any of embodiments 1-8, wherein the administering is before an upcoming insult.
10. A method of embodiment 9, wherein the upcoming insult is a scheduled insult.
11. A method of embodiment 10, wherein the scheduled insult is surgery or chemotherapy.
12. A method of any of embodiments 1-11 wherein the promoting alleviates a symptom of neurodegeneration.
13. A method of embodiment 12 wherein the neurodegeneration is a peripheral neuropathy.
14. A method of promoting neural growth and/or neural survival including contacting a neural cell or nerve with a therapeutically effective amount of an IL-17c protein thereby promoting neural growth and/or neural survival.
15. A method of embodiment 14, wherein the neural growth and/or neural survival is evidenced by increased neural cell survival, increased neurite growth (axon or dendrite), neurite guidance (axon or dendrite), and/or increased innervation
16. A method of embodiment 14 or 15, wherein the IL-17c protein includes SEQ ID NO: 1.
17. A method of any of embodiments 14-16, wherein the neural cell or nerve is from the peripheral nervous system.
18. A method of any of embodiments 14-17, wherein the neural cell or nerve is from a sensory or motor neural cell or nerve.
19. A method of any of embodiments 14-18, wherein the neural cell or nerve is within the dermis of a subject.
20. A method of embodiment 19, wherein the subject is a subject in need of the promoting neural growth and/or neural survival.
21. A method of any of embodiments 14-20, wherein the promoting alleviates a symptom of neurodegeneration.
22. A method of any of embodiments 14-20, wherein the neurodegeneration is a peripheral neuropathy.
23. A composition including a therapeutically effective amount of an IL-17c protein and a pharmaceutically acceptable carrier.
24. A composition of embodiment 23, wherein the IL-17c protein includes SEQ ID NO: 1.
25. A composition of embodiment 23 or 24, wherein the pharmaceutically acceptable carrier includes a topical carrier.
26. A composition of any of embodiments 23-25, wherein the pharmaceutically acceptable carrier is selected from an aqueous carrier, an oil-based carrier, a fat-based carrier, a fatty alcohol-based carrier, or a combination thereof.
27. A kit for promoting neural growth and/or neural survival, the kit including a therapeutically effective amount of an IL-17c protein and instructions for administering the therapeutically effective amount of the IL-17c protein to a subject.
28. A method of promoting neural growth and/or neural survival including contacting keratinocytes with a therapeutically effective amount of a virus, a TLR2 ligand and/or a TLR5 ligand thereby promoting neural growth and/or neural survival.
29. A method of promoting neural growth and/or neural survival including contacting keratinocytes with a virus, a TLR2 ligand and/or a TLR5 ligand in an amount sufficient to elicit release of a therapeutically effective amount of IL-17c thereby promoting neural growth and/or neural survival.
30. A method of embodiment 28 or 29 wherein the virus is HSV, the TLR2 ligand is peptidoglycan or the TLR5 ligand is flagellin.
31. A method of embodiments 28-30, wherein the neural growth and/or neural survival is evidenced by increased neural cell survival, increased neurite growth (axon or dendrite), neurite guidance (axon or dendrite), and/or increased innervation within 5 inches of the contacted keratinocytes.
32. A method of embodiments 28-31, wherein the neural cell or nerve is from the peripheral nervous system.
33. A method of embodiments 28-32, wherein the neural cell or nerve is from a sensory or motor neural cell or nerve.
34. A method of embodiments 28-33, wherein the neural cell or nerve is within the dermis of a subject.
35. A method of embodiment 34, wherein the subject is a subject in need of the promoting neural growth and/or neural survival.

36. A method of any of embodiments 28-35, wherein the promoting alleviates a symptom of neurodegeneration.
37. A method of any of embodiments 28-36, wherein the neurodegeneration is a peripheral neuropathy.

As stated, IL-17c proteins include SEQ ID NO: 1 and biologically active analogues thereof (e.g., variants, D-substituted analogs and modifications). Reference to other active ingredients also includes biologically active analogues of the referenced active ingredient.

Example 1

Introduction. Keratinocytes, immune cells and nerve fibers are interconnected anatomically and functionally in skin (Chuong et al., 2002; Misery, 1997). Herpes simplex virus types 1 and 2 (HSV-1 & HSV-2) have evolved strategies to exploit this system for recurrent infection. After primary infection at the site of acquisition (mouth and genitals), viruses travel retrogradely via axons to cell bodies of peripheral sensory neurons where they establish latency. Reactivation from latency involves anterograde movement to sites near the original site of entry for replication and transmission (Roizman and Whitley, 2013). Human recurrent HSV-2 infection is frequent and often clinically asymptomatic (Johnston et al., 2012; Schiffer et al., 2013; Wald et al., 1997). While sensory anesthesia may precede or accompany HSV-2 reactivation, reports of such peripheral nerve damage or neuropathy are extremely rare among patients with HSV-2 recurrent infection, a clinical observation that distinguishes it markedly from Varicella Zoster Virus infection, where nerve destruction and neuropathy are well recognized. It is unclear how peripheral nerves maintain their function in spite of frequent HSV-2 reactivation over time. In fact, there is controversy whether peripheral nerve damage is associated with human HSV-2 reactivation.

The interleukin 17 (IL-17) family consists of 6 members (IL-17a, IL-17b, IL-17c, IL-17d, IL-17e and IL-17f) (Gaffen, 2009; Gaffen, 2011). To date IL-17c has been identified as an epithelial cell derived cytokine that regulates innate immune function (Ramirez-Carrozzi et al., 2011; Song et al., 2011) and promotes inflammation in psoriasis (Johnston et al., 2013; Ramirez-Carrozzi et al., 2011). Here it is reported that both keratinocytes and neurons produce IL-17c in response to HSV-2 infection and IL-17c functions as a neurotrophic factor that can provide a survival signal to protect neurons from apoptosis during HSV infection and most importantly stimulates peripheral nerve growth.

Methods. Study participants. Healthy, HSV-2 seropositive adults were recruited at the University of Washington Virology Research Clinic in Seattle, Wash. HSV-2 serostatus was determined by Western blot as previously described (Koutsky et al., 1992); all participants were HIV seronegative and biopsy procedures were conducted as described previously (Peng et al., 2009; Zhu et al., 2007). The biopsy protocol was approved by University of Washington Human Subjects Review Committee and all participants provided written consent. All samples were immediately placed on dry ice and stored at −80° C. until processing.

Purification of keratinocytes from genital skin biopsies. A rapid immunofluorescent staining method (<15 minutes) was utilized to identify CD8+ T cells located at the dermal epidermal junction (DEJ) from skin biopsies (Peng et al., 2012; Zhu et al., 2013). Then the Zeiss PALM Microbeam laser capture micro-dissection (LCM) system was used to cut and catapult individual keratinocytes above the basement membrane to designated tubes in a completely automated process. Between 50 and 100 cells were captured per skin biopsy and 1 to 10 ng of isolated total RNA was processed for gene expression analysis via the Illumina array platform.

RNA extraction, amplification and hybridization of cDNA to Illumina beadarrays. Total RNA from LCM-captured keratinocytes was extracted using PicoPure RNA isolation kits following the manufacturer's protocol (Applied Biosystems, CA, USA). The quality of total RNA was analyzed by Agilent pico chips and RNA with a quality index (RIN) above 5 was used. Total RNA (0.5-1 ng) was then used for cDNA synthesis using the Ovation Pico RNA Amplification System (NuGEN, CA, USA). The size distribution of cDNA was analyzed by Agilent Technologies nano chips and the amplified cDNA had a Gaussian distribution with an average size of 200 bp. The cDNA was biotin-labeled per the NuGEN protocol and labeled cDNA (750 ng) was hybridized to Illumina HT-12 beadarrays in the Shared Resource Genome Center at Fred Hutchison Cancer Research Center per the manufacturer's instructions.

Analysis of beadarray data. Raw data were imported to GenomeStudio (V2010.3, Illumina). Control summaries were generated to analyze the quality of hybridization. Data passing this initial quality control step were normalized using Cubic Spline with background subtraction. Normalized data were exported to R and differentially expressed genes between keratinocytes from control biopsies and those from healed skin biopsies were selected using Genefilter, a Bioconductor package. The differentially expressed genes were analyzed using an unsupervised hierarchical clustering method (Clustering method: UPGMA [weighted average] and similarity measure: euclidean distance) using SpotFire DecisionSite for functional genomics (Version 9.1.2). Enriched functional categories and network analyses for differentially expressed genes were performed using Ingenuity Pathway Analysis (IPA 8.8). The GOMiner program was used to annotate all the 20,818 genes on Illumina Human HT-12 beadarrays. An annotation database was constructed in Microsoft Access using exported tables from GOMiner and genes that were annotated to the following GO terms: cytokine/chemokine/growth factor activity and cytokine/chemokine/growth factor receptor activity were exported for further analysis in SpotFire.

Viral stocks. Viral stocks utilized in this study include HG52 (HSV-2); HSV-1 strains are KOS and ICP8 mutant (ICP8mu) (kindly provided by Dr. David Knipe, Harvard Medical School, Boston, Mass.), ICP0 mutant (ICP0mu) and ICP22 mutant (ICP22mu) (kindly provided by Dr. William P. Halford, Southern Illinois University School of Medicine, Springfield, Ill.) and K26 which contains VP26-GFP fusion gene (a generous gift from Dr. Prashant Desai, Johns Hopkins University, Baltimore, Md.). Viral titers were determined by titration in Vero cells.

Cell cultures. Primary keratinocytes were purchased from Lifeline Cell Technology (Frederick, Md.). Cells were cultured in DermaLife® Basal Medium with DermaLife K LifeFactors (Cat #LS-1030) as recommended by the manufacturer. Acyclovir stock solution was prepared in DMSO at 6.76 mg/ml (30 mM) (Sigma) and diluted 1:1000 for use on primary keratinocytes (30 µM). To UV treat a virus stock, HG52 virus stock was spread on a tissue culture grade 60 mm petri dish.

With the petri dish lid off a UV light source was placed 2 inches above virus for 30 minutes. UV-treated virus was stored at −80° C. for later use. For TLR2 and TLR5 stimulation, cells were treated with peptidoglycan (PGN) at 2 µg/ml or flagellin at 0.1 µg/ml (PGN and flagellin are from InvivoGen and Sigma, respectively). The TLR2 neutralizing antibody is from InvivoGen. To block IL-17c signaling, keratinocytes were treated with a neutralizing antibody for human IL-17RA (mouse monoclonal antibody) and matching mouse control IgG (R&D systems) (2 µg/ml) for 1 hour before HSV infection.

Primary MCN were purchased from Life Technologies and cultured as recommended by the manufacturer. To block IL-17c signaling, cells were treated with a neutralizing antibody for IL-17RA (rat monoclonal antibody) and matching rat control IgG (R&D systems) (2 µg/ml) for 1 hour before K26 infection. Murine IL-17c (mIL17c) was synthesized and purified in Fred Hutchinson Research Center shared resource facility. To detect apoptosis during HSV infection of mouse primary neurons, cells were stained with an antibody for cleaved caspase 3 (Cell Signaling Technology) according to the manufacturer's methods.

Human SH-SY5Y neuroblastoma cells were obtained from the ATCC. The SH-SY5Y neuroblastoma cell lines were maintained in 1:1 mixture of ATCC-formulated EMEM and F12 media containing 15% (v/v) heat-inactivated FBS without antibiotics. SH-SY5Y cells were induced to differentiate up to 7 days with 50 µm all-trans retinoic acid (ATRA; Sigma) in 1:1 mixture EMEM/F12 media supplemented with 5% (v/v) FBS without antibiotics. They were monitored daily by phase-contrast microscopy for the appearance of elongated neurites. A differentiated cell was defined as a cell with a neurite length greater than the length of the cell body (on average greater than 10 µm in length) and expressing β-tubulin III (Abcam).

Isolation of Human Fetal Dorsal Root Ganglia and Sensory Neurons. Human fetal spinal cords were isolated from first and early second trimester aborted specimens, obtained from the Laboratory of Developmental Biology in full compliance with the ethical guidelines of the National Institutes of Health and with the approval of the University of Washington institutional review boards for the collection and distribution of human tissues for research. The Laboratory of Developmental Biology obtained written consent from all tissue donors. The tissue was briefly washed in Hanks' balanced salt solution (HBSS) and transported in Hibernate E at 4° C. prior to isolation of DRG.

All ganglia were dissected under sterile conditions, dissected free of fascia and connective tissue, and collected in DMEM and digested in 0.25% trypsin solution for 30 min at 37° C., washed in culture medium containing 10% FBS, and then triturated into a single-cell suspension with a fire-polished glass Pasteur pipet. Cells were resuspended in Neurobasal media (NB, Life Technologies) supplemented with B27 and 0.5 mM Glutamax (with antibiotics) and counted with trypan blue assay. Cell suspensions were plated in Poly-D-Lysine and Laminin coated 8-well chamber slides (BD/Corning) in NB/B27 media supplemented with 50 ng/ml human β-NGF (Millipore) and incubated overnight at 37° C. For each experiment, the cells were washed twice with basal media before addition of PBS or recombinant human IL-17c (200 ng/mL, ebioscience; or internally-generated human IL-17c). Cells with neurites were scored as neurons. Identification of the cells as neurons was confirmed by showing reactivity on the neurites with monoclonal antibody for PGP9.5.

Culture of neurons in microfluidic chambers. Microfluidic chambers (Xona Microfluidic, LLC) were autoclaved and bonded into FluoroDish (World Precision Instruments, Inc.) using a laboratory Corona treater (Electro-Technic Products, Inc.). Microfluidic chambers were coated with 1% (v/v) polyethylenimine (PEI) for 10 mins and 0.1% (v/v) glutaraldehyde for 30 mins to provide adhesion to the collagen gels. Rat tail collagen I (Gibco) was perfused through microfluidic chambers at a concentration of 5 µg/cm$^2$. Twenty microliters of 2,000,000 cells/mL differentiated SY5Y cells were seeded into the soma channel.

After 10 mins, 50 µl of culture media was added into each soma reservoir and 70 µl of culture media with 200 ng/ml IL-17c or NGF or same volume of PBS was added into each distal reservoir. Half of the growth media was changed every other day. Ten days later, cultures were fixed and stained with a PGP9.5 antibody.

For human primary fetal neuron culture, 3-channel microfluidic chambers (Xona Microfluidic, LLC) were autoclaved and bonded onto clean coverslips (Corning) using a plasma cleaner (Harrick Scientific, Inc.). The chambers were sterilized with 70% ethanol and then coated with 0.5 mg/mL poly-d-lysine (Corning) and 10 µg/ml mouse laminin (Life Technologies). Dissociated human fetal DRG neurons were plated into the middle channel at a density of 100,000 cells/chamber. After 4 days, 200 ng/mL IL-17c was added into the right channel to generate a gradient of IL-17c in the soma (middle) channel. Half of the growth media was changed every other day. Sixteen days later, cultures were fixed and stained.

Time-lapse microscopy. Transmitted light time lapse microscopy of neuroblastoma cells in microfluidic devices was performed on a Nikon Ti inverted microscope fitted with a Nikon 40x/0.9 S Fluor objective (Nikon Instruments Inc., Melville, N.Y.) and a Photometrics Coolsnap HQ scientific grade CCD camera. The devices were mounted inside a Chamlide stage top incubator (Live Cell Instrument, Seoul, Korea) maintained at 37° C. and 5% $CO_2$ and focus was maintained with Nikon's proprietary Perfect Focus system. Bright field images were collected at 5 min intervals for 16 hours.

Long term kinetic imaging of cultivated human neurons grown in 8-well chamber slides inside a conventional tissue culture incubator was performed with an Incucyte microscope system (Essen Bioscience Inc., Ann Harbor, Mich.) fitted with a Nikon 10x/0.3 Plan Fluor objective. Bright field images were collected at one-hour intervals. Four fields of view were imaged in phase contrast for each well, and average neurite length and number of branch points were measured with the Incucyte neuro-track image analysis software module.

Slide scanning and cytometric analysis. To quantify IL-17c+ cells, 30,000 keratinocytes or 80,000 MCN were cultured overnight or for 3 days in 8 well chamber slides before IL-17c pre-treatment and K26 infection (MOI of 2 and 5 for keratinocytes and MCN, respectively). Human keratinocytes were treated with human IL-17c (hIL-17c) (eBioscience) at 200 ng/mL in the presence of human IL-17RA neutralizing antibody (2 µg/mL) or matching control mouse IgG (2 µg/mL) for 12 hours before K26 infection. MCN were pretreated with murine IL-17c (mIL-17c) at 20 ng/mL in the presence of murine IL-17RA neutralizing antibody (2 µg/mL) or matching control rat IgG (2 µg/mL) for 24 hours before infection. Slides were scanned on a Tissuefax microscope system (Tissuegnostics GmbH, Vienna, Austria) including a Zeiss Imager Z2 upright fluorescence microscope, motorized Marzhauser stage with 8-slide capacity, and PCO pixelfly QE CCD camera. System operation was controlled by Tissuefax software which provided automated large area acquisition with image stitching and autofocus. Images were acquired with a Zeiss Plan Apochromat 10x/0.45 objective. Zeiss fluorescence filter sets for DAPI, FITC (for GFP) and Cy5 (for IL-17c and cleaved caspase 3) were used.

Image analysis was performed with Tissuegnostics TissueQuest software. Whole slide scans were imported into TissueQuest. Images were segmented and cells were identified by setting appropriate intensity thresholds and cell size parameters for all channels. Live cells were identified and counted based on nuclear channel staining (DAPI). Average staining intensity of the green and far red channels was measured for all segmented objects (cells). Typically, a cell mask including nucleus and cytoplasm was used. In some cases where the staining was predominantly cytoplasmic and cell size and shape was very heterogeneous, a ring mask derived from the nuclear mask was used to sample average staining intensity in the cytoplasm. Once all cell data had been obtained, intensity values for the desired channels were plotted for all cells as density plot using sm package in R and appropriate cut-offs were set to obtain counts and percentages of positive cells. DAPI+ cells were counted as live neurons and cleaved caspase 3+ cells were counted as neurons under apoptosis. The accuracy of the algorithms was verified by performing manual counts of selected regions and comparing them with the output of the TissueQuest software; there was good agreement between the two methods.

Immunofluorescent staining. The staining methods were previously described (Peng et al., 2012; Zhu et al., 2009; Zhu et al., 2007; Zhu et al., 2013). The antibodies for staining were purchased from the following sources: IL-17c antibody (mouse monoclonal, R&D); IL-17RE antibody (rabbit polyclonal, Sigma); IL-17RA antibody (rabbit monoclonal, LifeSpanBioSciences); NCAM antibody (mouse monoclonal, Bechman Coulter); PGP9.5 (Abcam); NF200 antibody (rabbit polyclonal, Sigma); Peripherin antibody (rabbit & mouse, Sigma); NF-κB and IRF-3 antibodies (rabbit polyclonal and mouse monoclonal, respectively, Santa Cruz); Cleaved caspase 3 antibody (rabbit polyclonal, Cell Signaling).

Quantitative RT-PCR (qRT-PCR) assay. Total RNA was extracted from human primary keratinocytes and mouse cortical neurons using Qiagen RNeasy mini kits. The cDNA was synthesized from total RNA using high capacity cDNA synthesis kits (Applied Biosystem). The TaqMan probes for ACTB, IL-17c, IL-17RE, NF-κB, IRF1, IRF3, IRF7, IFI16 and PML were ordered from Applied Biosystems (Inventoried primer-probes). The gene expression was normalized to ACTB.

Semi-automated measurements of nerve fiber density in skin biopsy. Tissue sections chosen from each biopsy were immunoassayed with polyclonal anti-neuronal cell adhesion molecule (NCAM/CD56, BioLegend, CA USA) antibody (1:100 dilution), using the Tyramide Signal Amplification (TSA; Invitrogen) method for fluorescence immunohistochemistry. Sections were analyzed and captured on Leica DMR at 20× magnification. Nerve fiber density (defined as mm/mm per section) across the entire dermal-epidermal Junction (DEJ) was calculated by using the application Simple Neurite Tracer on 2D images. This plugin is free software, licensed under the GNU GPL v3 and based on the public domain image processing software Fiji Image J. The software and step-by-step instructions are available online. Briefly, to trace a nerve fiber (neuronal path) both the starting and end points or successive points along the midline of a neural process were selected and pixels generated converted to µm.

Fluorescent in situ Hybridization (FISH). Fresh frozen skin biopsies or fetal DRG were cryosectioned into 10 µm slides, fixed with chilled 10% buffered formalin (Fisher), dehydrated in ethanol series, pretreated with protease K and hybridized using RNAscope multiplex fluorescent assay (Advanced Cell Diagnostics, ACD), according to the manufacturer's instruction. The probes used were: human Il17RE (ACD), human TUBB3-C2 (ACD), positive control PPIB (ACD) and negative control DapB (ACD).

Figure 1A:
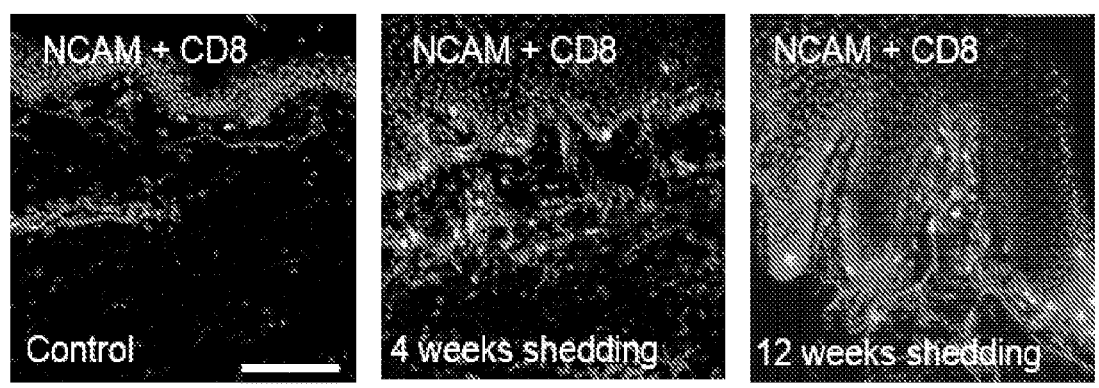
FIGS. 1A-1D. Nerve fiber growth during HSV reactivation. 1A. Nerve fibers in skin biopsies at time of subclinical HSV-2 reactivation (shedding) are stained for NCAM. An increased number of NCAM+ nerve fibers in the area just below the dermal epidermal junction, the site of HSV-2 reactivation, is seen as compared to control biopsy obtained from contralateral genital skin. Cells were co-stained with an anti-CD8a antibody and DAPI. Scale bar: 50 µm. 1B. Comparison of length and width of NCAM+ nerve fibers between biopsies obtained at time of HSV-2 shedding and contralateral control biopsies. Each line represents one individual (n=4). 1C. The difference of nerve fiber length between biopsies and contralateral controls at the time of shedding (n=4) versus biopsies in which no HSV reactivation was detected (n=8). P-value is derived from 2 samples t-test with unequal variance. 1D. NCAM+ nerve fibers express NGFR and intermediate filaments (peripherin and NF200). Tissue of 4 weeks post healed asymptomatic shedding skin biopsies was double stained with anti-NCAM and NGFR, peripherin or NF200 antibodies. Scale bar: 50 µm.
Figure 1B:
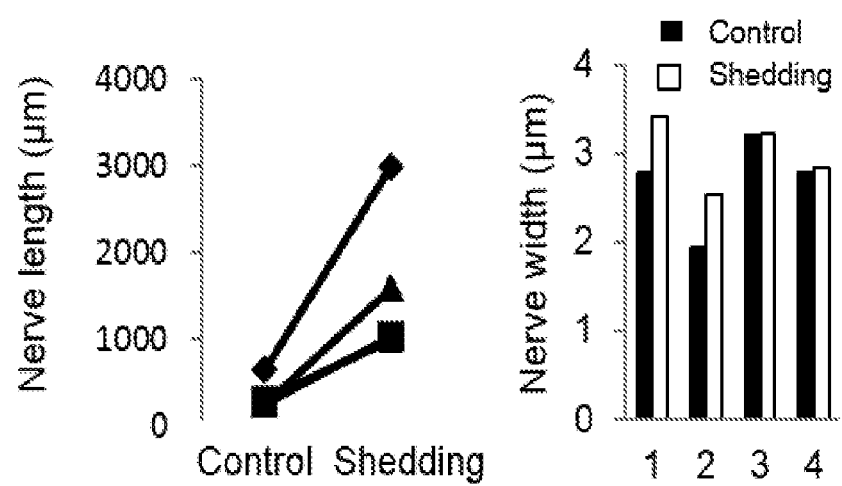
Figure 1C:
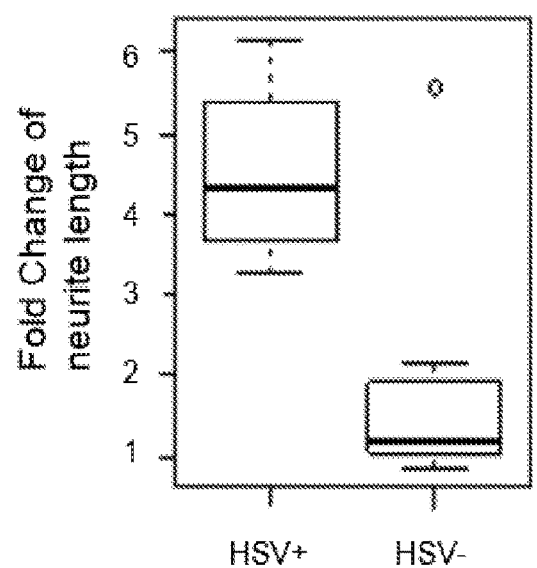

Results. Interaction of keratinocytes and nerve fibers via IL-17c/IL-17RE during human recurrent herpes simplex virus 2 infection. There is a spatially close proximity among cutaneous nerve endings, basal keratinocytes and CD8+ T cells in biopsy tissues taken during HSV-2 asymptomatic reactivation (Zhu et al., 2009; Zhu et al., 2007; Zhu et al., 2013). To explore the impact of recurrent HSV-2 infection on peripheral nerves, the length and width of nerve fibers positive for neuronal cell adhesion molecule (NCAM) was measured in genital skin biopsies taken at the time of asymptomatic reactivation and these measurements were compared to control genital skin biopsies in contralateral sites taken from areas without HSV reactivation. Peripheral nerve fibers in tissues undergoing HSV asymptomatic shedding had a much higher density compared to nerve fibers detected in control skin (FIG. 1A). Nerve fibers in skin biopsies showing recent HSV-2 reactivation were much longer on average, as compared to those in matching controls (n=4); while the width of nerve fibers was similar (FIG. 1B). The increase in nerve fiber length in genital skin biopsies during viral asymptomatic reactivation relative to their matching control biopsies (n=4) was 4 fold greater than those without detectable shedding (n=8) (FIG. 1C).

Figure 1D:
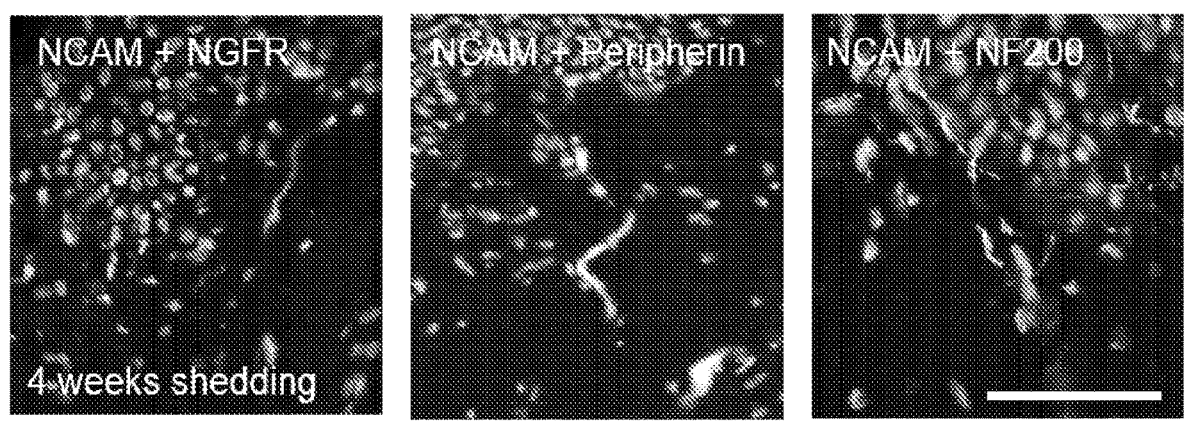

NCAM+ nerve fibers in post healed skin biopsies also co-expressed the low-affinity nerve growth factor receptor (NGFR). Both peripherin+ and NF200+ nerve fibers were found to be present in the papillary dermis close to the epidermis (FIG. 1D). These results suggest that neurotrophins might be released locally to stimulate nerve growth and/or repair nerve endings in response to HSV-2 reactivation.

Figure 2A:
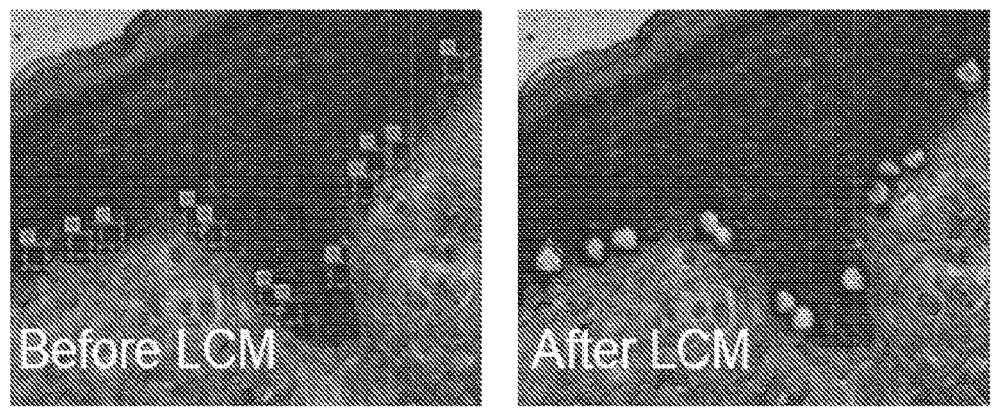
FIGS. 2A-2C. Recurrent HSV-2 reactivation induces IL-17c expression in keratinocytes. 2A. Isolation of keratinocytes above basement membrane by laser capture microdissection (LCM). 2B. HSV infection in keratinocytes induced IL-17c expression in vivo. Comparison of expression of cytokines/chemokines (top panel) and six different members of IL-17 (bottom panel) in keratinocytes isolated from lesion and post healed skin (Asymptomatic shedding) biopsies to those from contralateral control biopsies. 2C. IL-17c protein expression in epidermal keratinocytes in skin biopsies during lesion and shedding (clinical quiescence 8 weeks shedding). IL-17c expression was detected by immunofluorescent staining with an anti-IL-17c antibody and nuclei stained with DAPI. Scale bar: 50 µm.
Figure 2B:
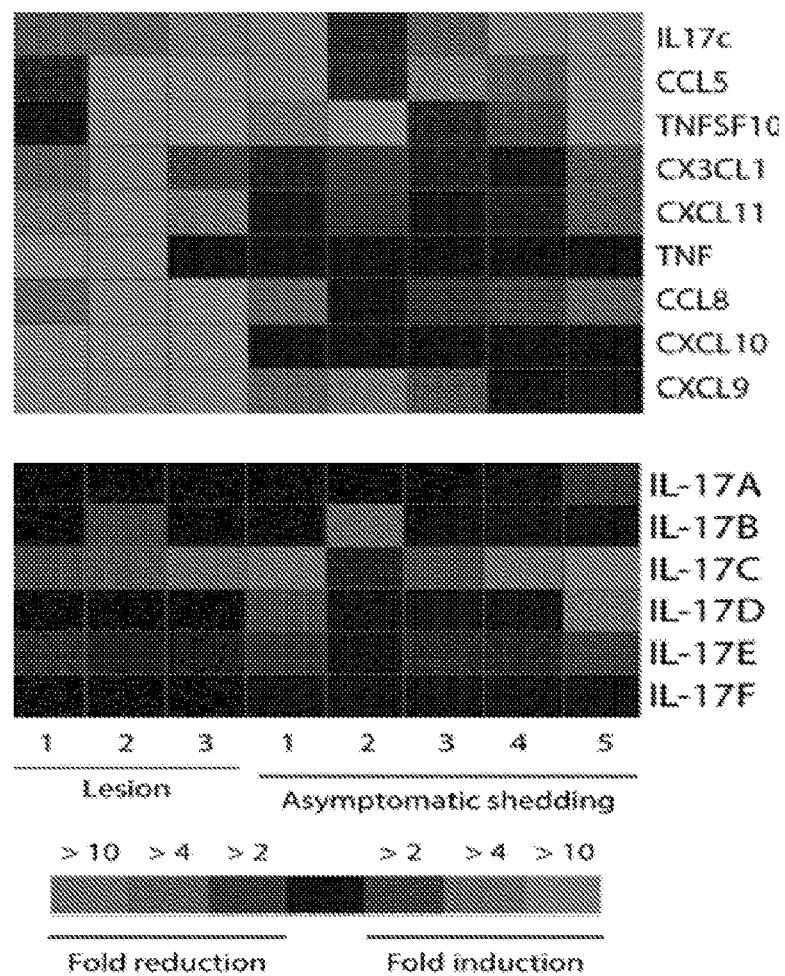
Figure 2C:
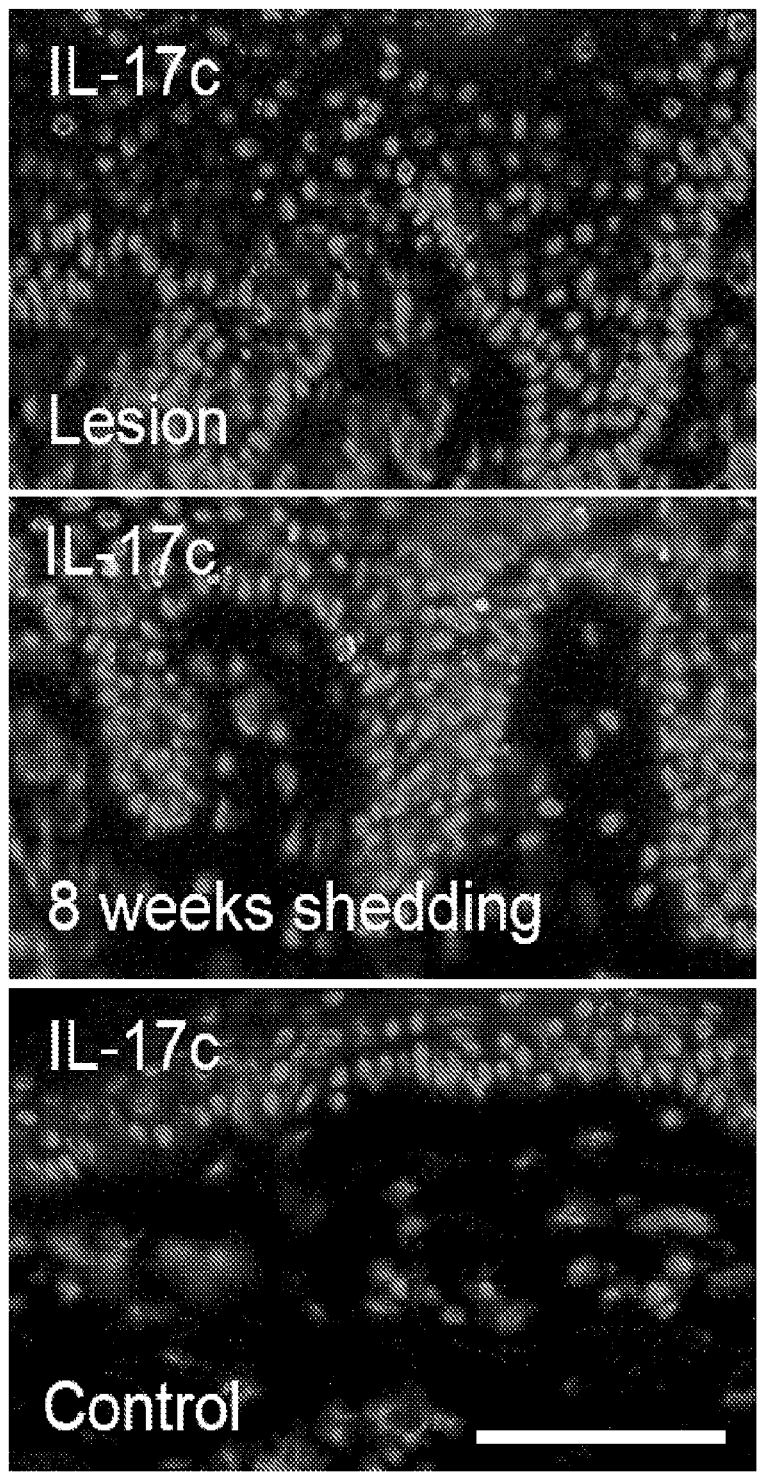
Figure 3:
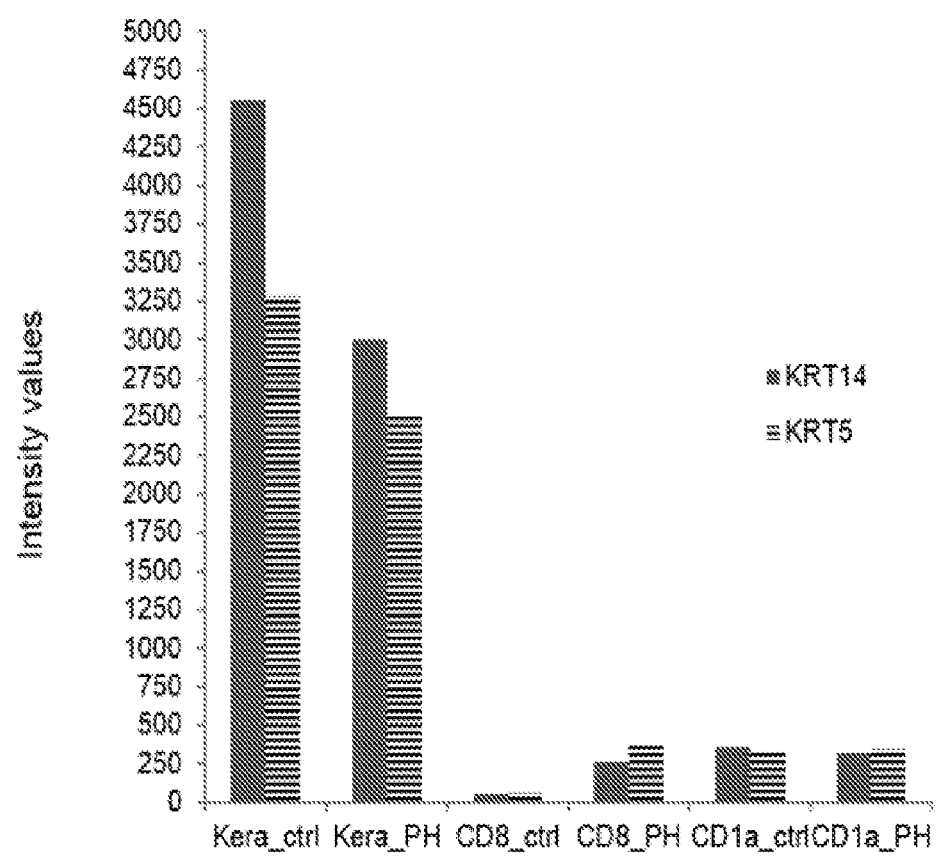
FIG. 3. Expression of keratin 5 (KRT5) and 14 (KRT14) in laser captured keratinocytes (Kera), CD8a+ CD8 T cells (CD8) and CD1a+ Langerhans cells (CD1) from control (ctrl) and post healed (PH) genital skin biopsies during recurrent HSV-2 infection. Y-axis: intensity values from normalized Illumina BeadArray data. The displayed values are the averages for keratinocytes (n=4), CD8a+ CD8 T cells (n=8) and CD1a+ Langerhans cells (n=8).

To evaluate the role(s) of keratinocytes in influencing nerve fiber density during recurrent HSV-2 infection, individual basal keratinocytes were selectively recovered by laser capture microdissection (LCM) from human genital skin biopsies at the time of acute lesion and subsequently at 4 or 8 weeks post healing as well as contralateral control biopsies from the same patients (n=4) and compared their transcriptional profiles (FIG. 2A). Expression of keratin 5 and 14, markers of basal keratinocytes in the human epidermis (Lloyd et al., 1995), was measured in isolated keratinocytes as well as CD1a+ Langerhans cells and CD8a+ T cells (FIG. 3) (Peng et al., 2012; Zhu et al., 2013). The isolated keratinocytes expressed approximately 10 times higher levels of keratin 5 and 14 than the other cell types, suggesting an enriched cell population. Illumina Human HT-12 beadarrays contain about 300 genes annotated as growth factor/cytokine/chemokine activity; 3 were significantly induced in keratinocytes isolated from HSV-2 lesion and post healed biopsies (IL-17c, CCL5 and TNFSF10) and 6 were up-regulated only in keratinocytes from lesions (CX3CL1, CXCL11, TNF-α, CCL8, CXCL10 and CXCL9) (top panel, FIG. 2B). Among the six related IL-17 family members, IL-17c, a predominantly epithelial-derived cytokine (Gaffen, 2009; Ramirez-Carrozzi et al., 2011; Song et al., 2011) was the only induced gene in keratinocytes during recurrent HSV-2 infection (bottom panel, FIG. 2B). Immunofluorescent staining indicated that IL-17c was expressed in a small population of keratinocytes exclusively in the epidermis in lesion and post healed skin biopsies with asymptomatic shedding but not in control biopsies (FIG. 2C).

Figure 4C:
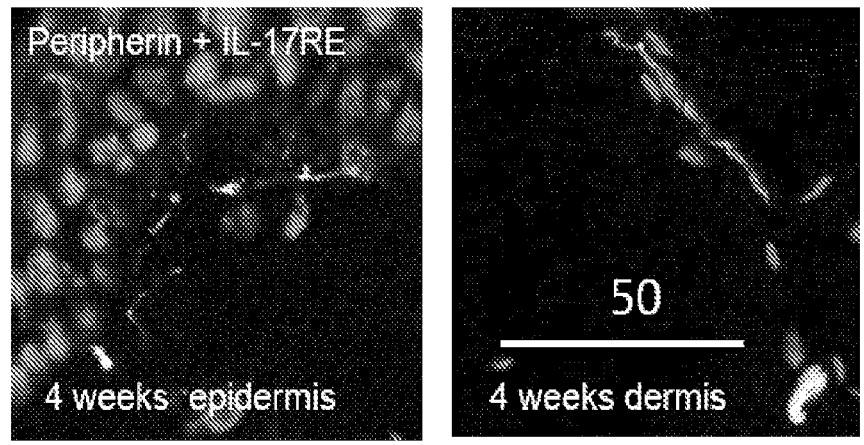
Figure 4D:
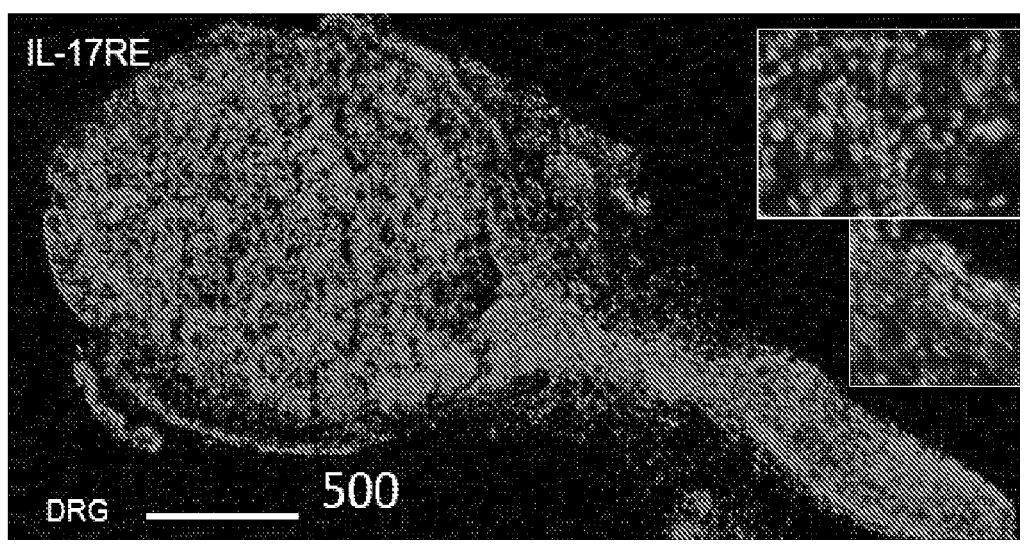
Figure 4E:
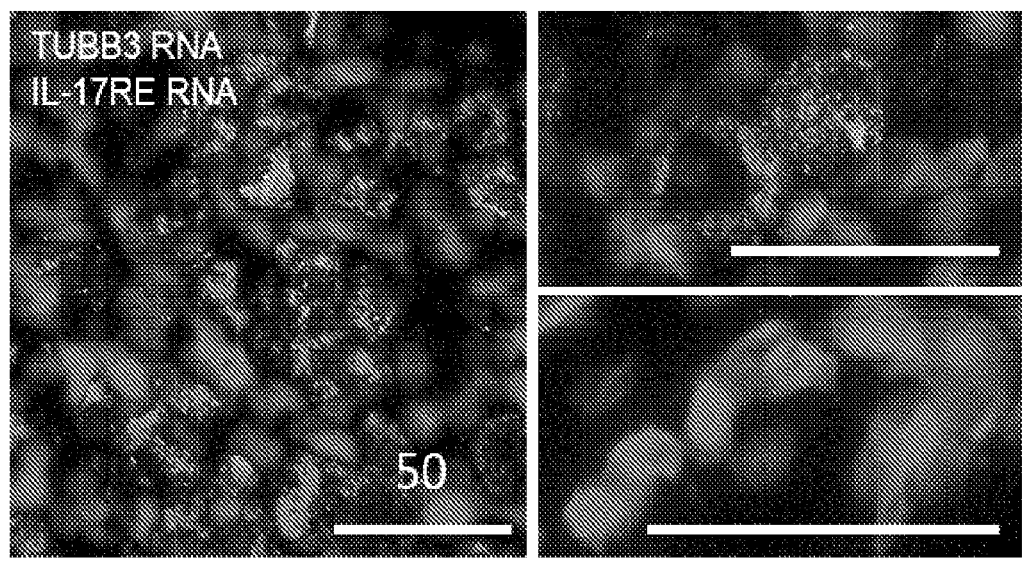
Figure 4F:
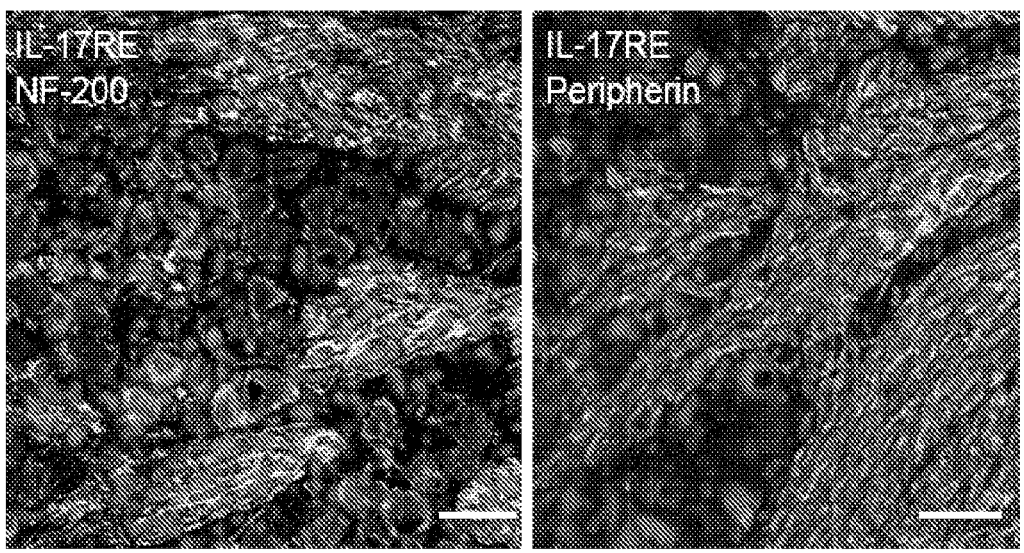

To identify the target cells of IL-17c during HSV-2 reactivation in vivo, immunofluorescent staining of IL-17RE, the orphan receptor for IL-17c (Chang et al., 2011; Ramirez-Carrozzi et al., 2011; Song et al., 2011), was performed. IL-17RE expression was found not on CD15+, CD8+ or CD4+ immune cells, markers of neutrophils and T cells, respectively, but on structures with elongated fiber like shapes and in keratinocytes (FIG. 4A). Dual staining for NCAM and IL-17RE and peripherin and IL-17RE showed that IL-17RE was detected on NCAM+ and peripherin+ nerve fibers in skin biopsies during active and asymptomatic HSV-2 infection (FIGS. 4B & 4C). To further investigate the neuronal expression of IL-17RE, the distribution of IL-17RE protein in fetal dorsal root ganglia (DRG) was examined. The expression of IL-17RE protein was detected in both soma and axonal regions of DRG (FIG. 4D). Dual in situ hybridization confirmed IL-17RE mRNA expression in beta-tubulin 111+ neurons and also in beta-tubulin 111-cells (FIG. 4E). IL-17RE was expressed in a subset of NF200+ or peripherin+ sensory neurons (FIG. 4F), consistent with its expression patterns observed in the genital skin (FIG. 1D). These findings indicate an abundance of IL-17RE in the peripheral neurons and provide evidence that IL-17c released from epidermal keratinocytes could interact with IL-17RE on nerve fibers in the dermal area during the process of HSV-2 reactivation.

HSV replication in human primary keratinocytes induces IL-17c expression. To test the hypothesis that HSV-2 reactivation could induce IL-17c in keratinocytes, human primary keratinocytes were cultured and evaluated for whether these cells would produce IL-17c in vitro in response to HSV infection over 12 hours. Peak induction occurred at 6 hours post-infection (p.i) and remained at elevated levels when infected with UV inactivated virus or acyclovir treatment (left panel, FIG. 5A). Next, tests were performed to determine whether HSV DNA replication activates IL-17c expression in keratinocytes because peak IL-17c induction coincided with early stages of HSV DNA replication, which is inhibited by both UV and acyclovir treatment. Keratinocytes were infected with HSV mutants containing gene deletions in the immediate-early (IE) genes ICP0 (ICP0mu) and ICP22 (ICP22mu), or early gene ICP8 (ICP8mu), a single-stranded DNA binding protein essential for HSV DNA replication, and the parental wild type HSV-1 strain (KOS). Over time, cells infected with IE gene mutants had significantly reduced levels of IL-17c. In contrast, ICP8mu induced IL-17c expression patterned similarly as the wild type KOS strain but at much higher levels (right panel, FIG. 5A). Immunofluorescent staining demonstrated IL-17c expression at the cell surface and in the cytoplasm in cultured keratinocytes infected with the HSV-2 strain HG-52 (left panel, FIG. 5B). Relative to mock infection, HG-52 infection at MOI of 1 and 10 induced 67% and 756% more IL-17c+ cells at 7 hours p.i, respectively (right panel, FIG. 5B). Thus, both HSV-1 and HSV-2 induce IL1-7c expression in human primary keratinocytes.

Peptidoglycan (PGN) and flagellin, bacterial ligands for TLR2 and TLR5, respectively, are known to stimulate IL-17c expression rapidly (Ramirez-Carrozzi et al., 2011). To understand whether the signaling pathways for IL-17c induction by HSV infection and TLR2/5 stimulation converge or are independent, IL-17c production was evaluated after combination HSV infection and PGN/flagellin treatment. A TLR2 neutralizing antibody blocked PGN-dependent IL-17c expression and the combination of HSV and PGN induced IL-17c in an additive manner (left panel, FIG. 5C). The combination of ICP8mu infection and flagellin treatment also additively induced IL-17c expression (right panel, FIG. 5C). These findings show that HSV infection and PGN/flagellin independently induce IL-17c expression in cultured human primary keratinocytes.

Figure 5A:
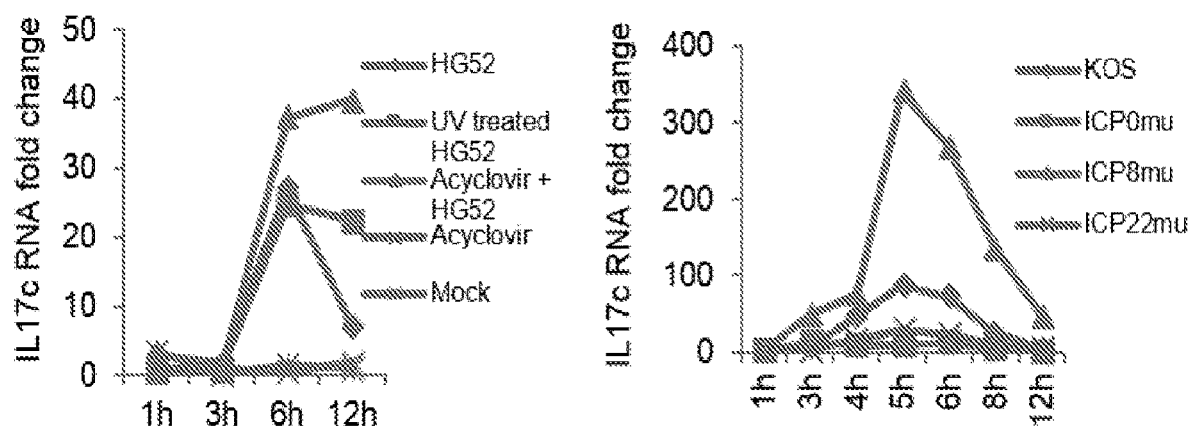
Figure 5B:
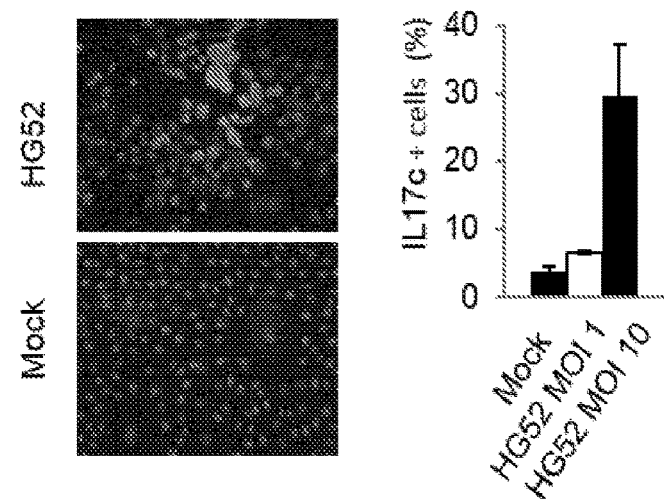
Figure 5C:
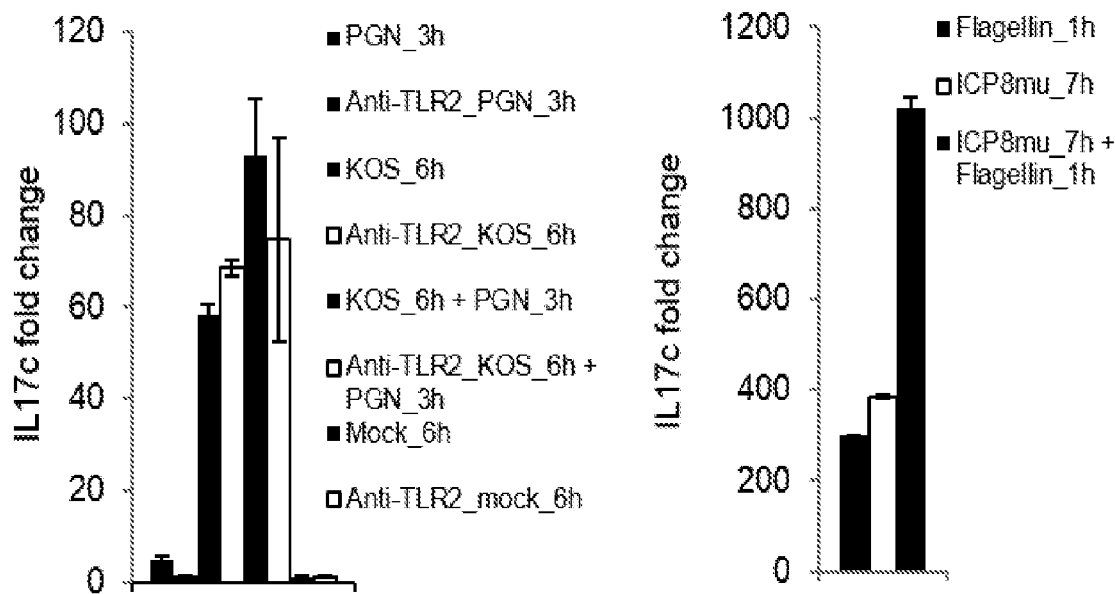
Figure 5D:
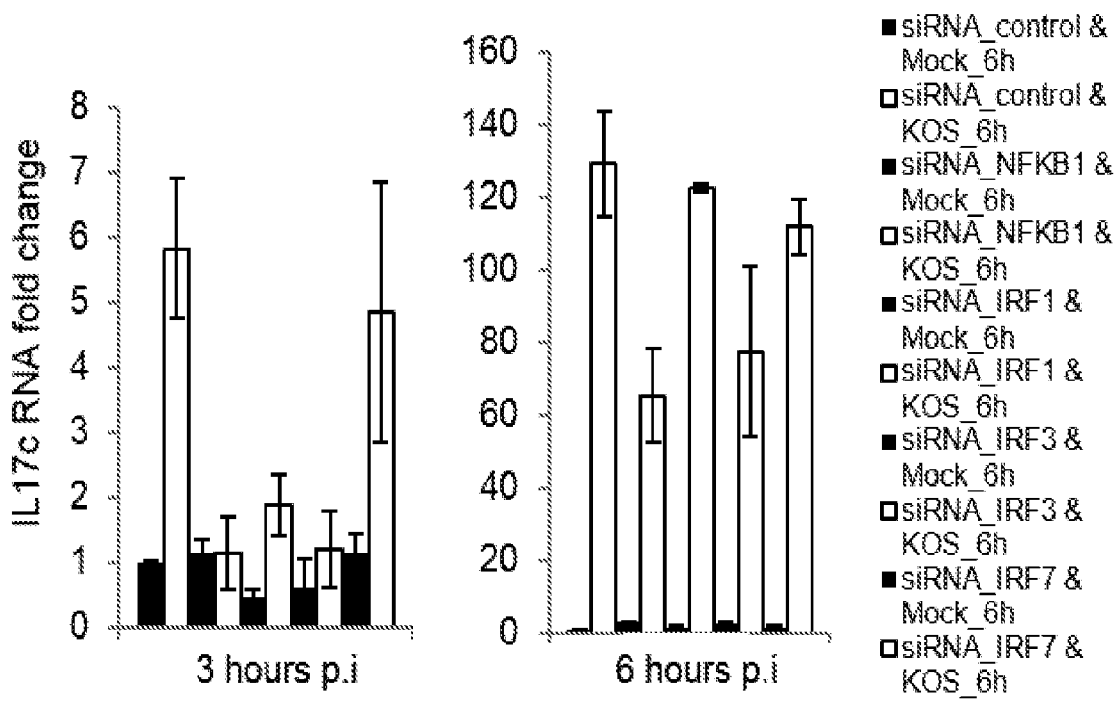
Figure 8A:
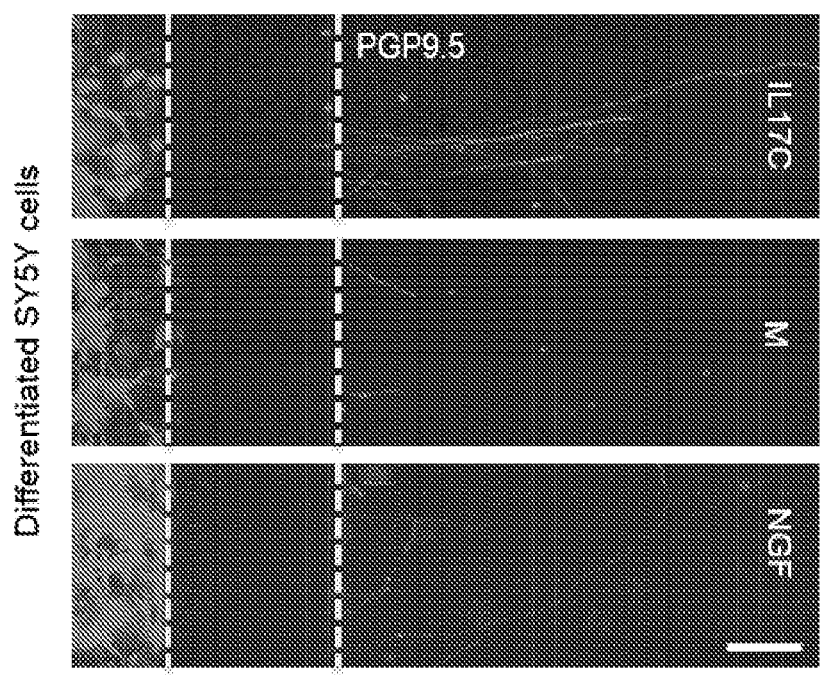
Figure 8B:
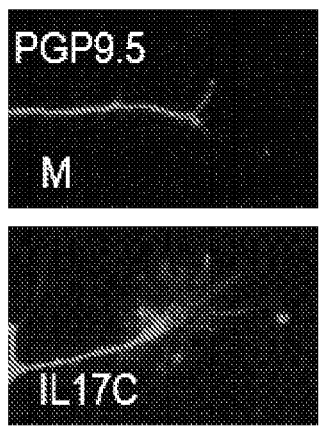
Figure 8C:
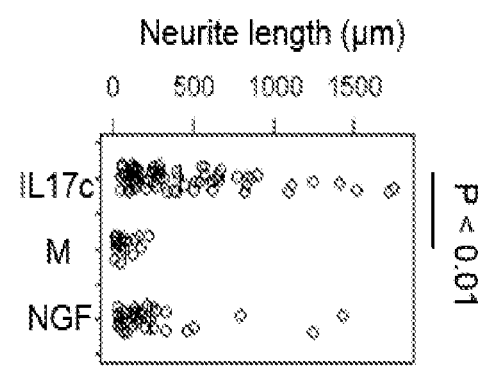
Figure 8D:
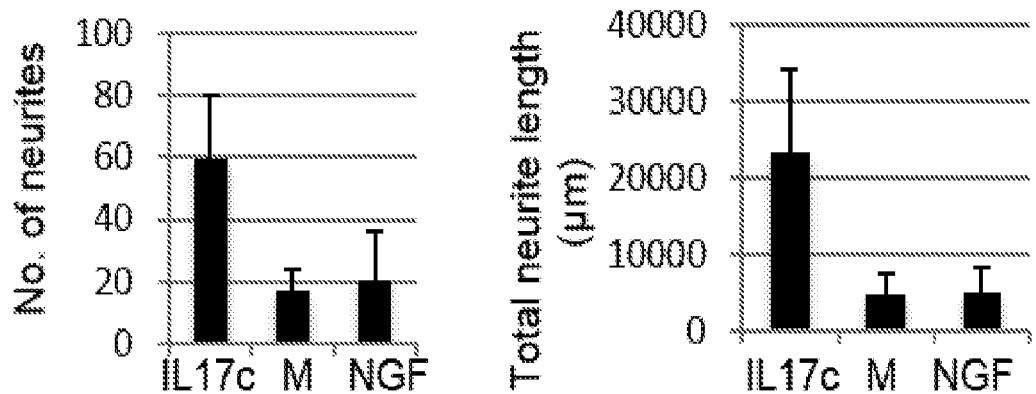

To identify transcription factors that mediate IL-17c induction, the transcriptional profiles of primary keratinocytes were analyzed. The keratinocytes displayed high levels of regulatory proteins involved in host innate defenses, such as NFKB1, IRF1, IRF3, IRF7, IFI16 and PML (data not shown) (Cuchet et al., 2011; Dev et al., 2011; Honda and Taniguchi, 2006; Orzalli et al., 2012). Gene specific siRNA transfection reduced expression of these transcription factors from 60 to 90% relative to control non-specific siRNA (FIGS. 6A & 6B). siRNA knock-down of NF-κB and IRF-3 blocked the IL-17c induction at 3 hours p.i and reduced its induction by about 50% at 6 hours p.i, suggesting that these two transcription factors mediate transcriptional induction of IL-17c during the early hours of HSV infection (FIG. 5D). HSV-induced IL-17c expression was not affected by siRNA knock-down of IRF7, IFI16 and PML, while it was significantly inhibited by IRF1 siRNA at 3 hours p.i yet had no effect on IL-17c induction at 6 hours p.i (FIGS. 6B & 8D).

IL-17c induces neurite growth of human neuroblastoma cells and primary sensory neurons. To understand biological functions of HSV induced IL-17c, the antiviral activity of IL-17c was examined. Blocking IL-17c signaling using a neutralizing antibody for IL-17RA or siRNA knock-down of IL-17-RE did not influence HSV gene expression or HSV titers in human primary keratinocytes (FIG. 7). Based on the lack of antiviral activity, the potential effect of IL-17c on neuronal functions was explored. First, the neurotrophic effects of exogenous IL-17c in differentiated SY5Y cells were tested. Retinoic acid induces cell cycle arrest and differentiation of SY5Y cells to a more neuron-like phenotype (Abemayor and Sidell, 1989). Using a two chamber microfluidic device, differentiated SY5Y cells were found to have visible neurites extending into microgroove channels after 24 hours in the IL-17c containing device (FIG. 8A). The growth cone of individual neurites appears to be larger in IL-17c containing devices (FIG. 8B). During the next 10 days, significantly more and longer neurites grew into the main channel with basal medium plus IL-17c as compared to medium only or medium plus NGF (FIGS. 8C & 8D). Taken together, the data show that IL-17c can stimulate neurite growth of cultured human neuroblastoma cells. These data were replicated using internally-generated Hutch human IL-17c protein.

Figure 9A:
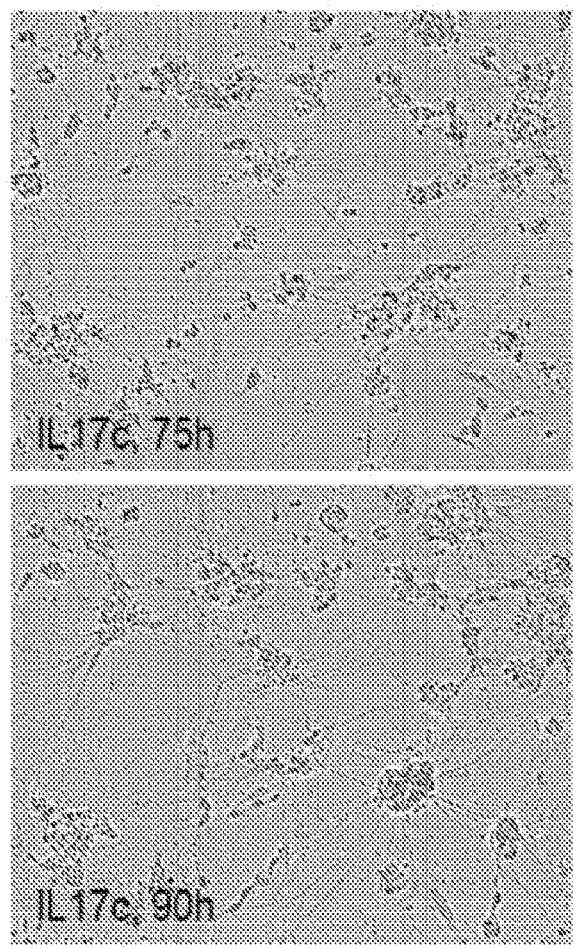
Figure 9B:
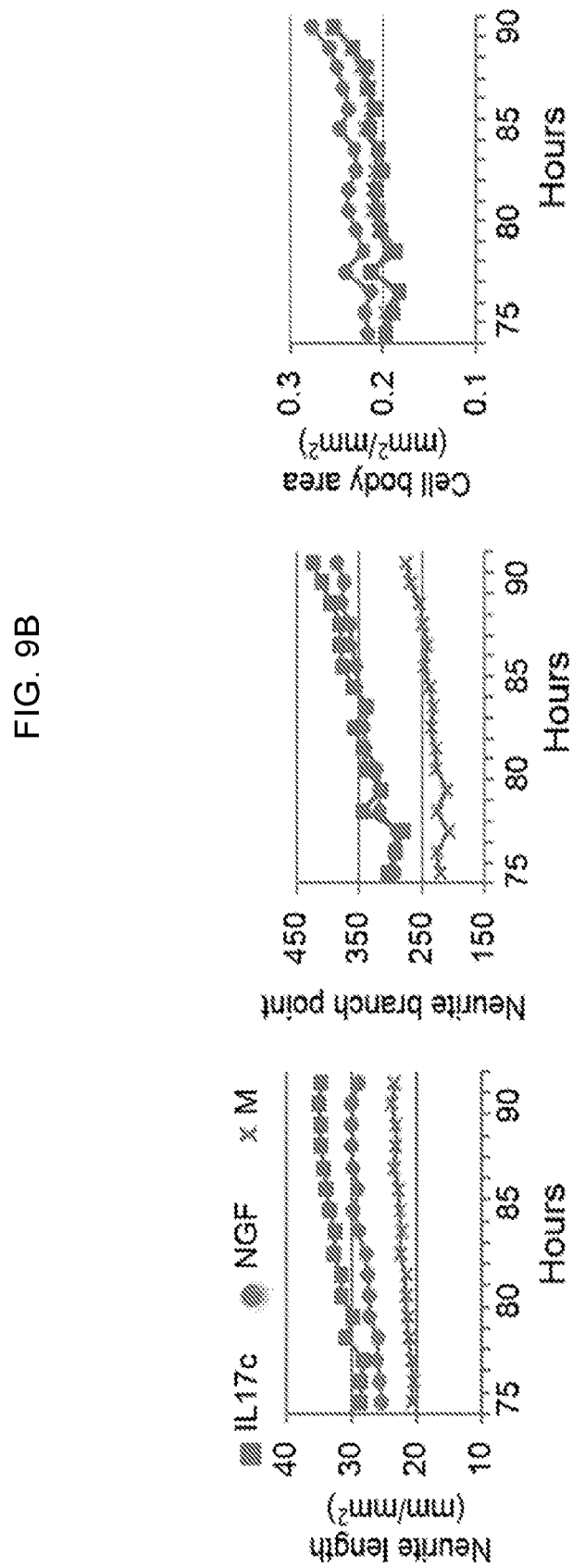
Figure 9C:
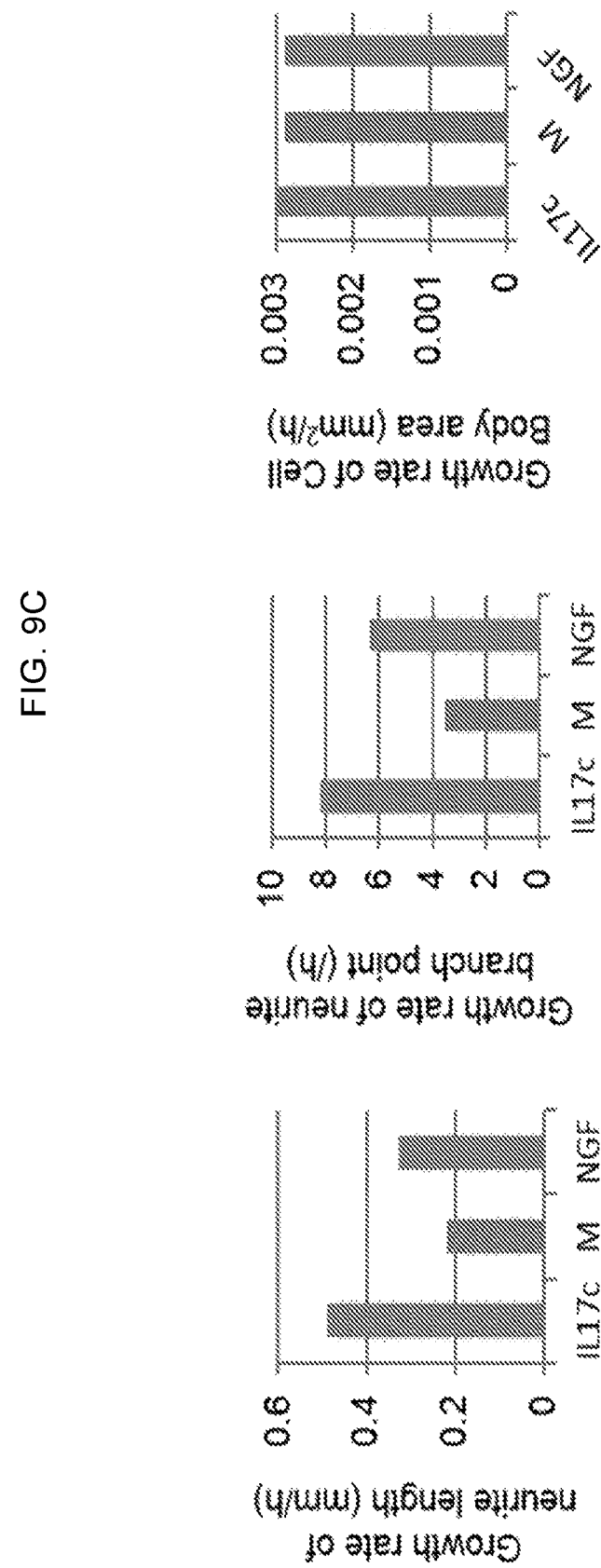
Figure 9D:
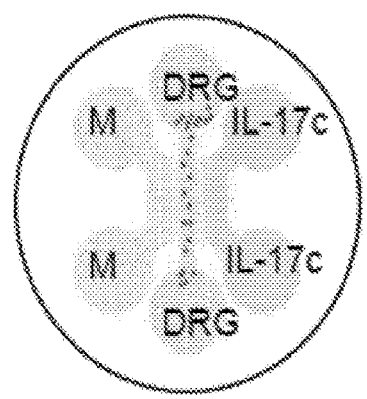
Figure 9E:
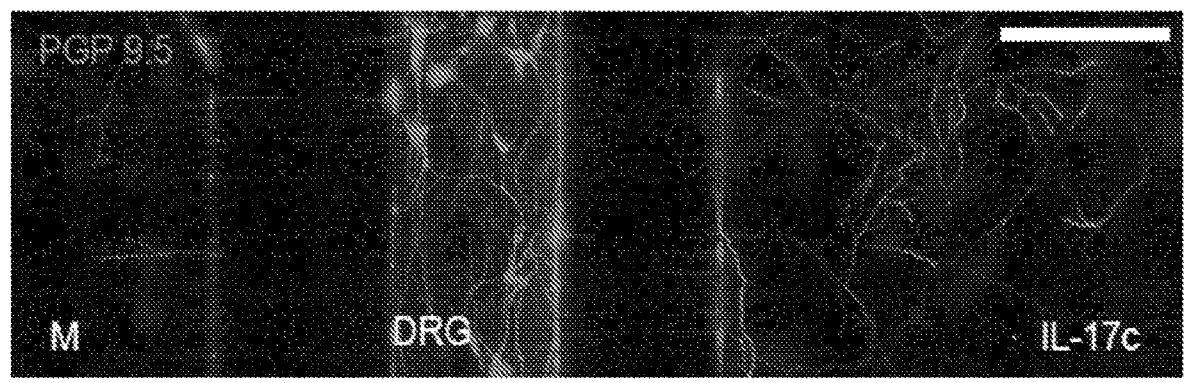
Figure 9F:
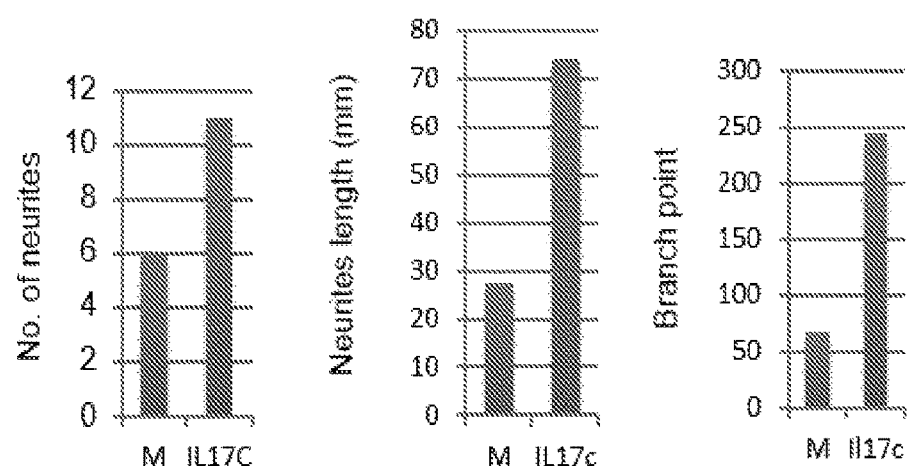
Figure 9G:
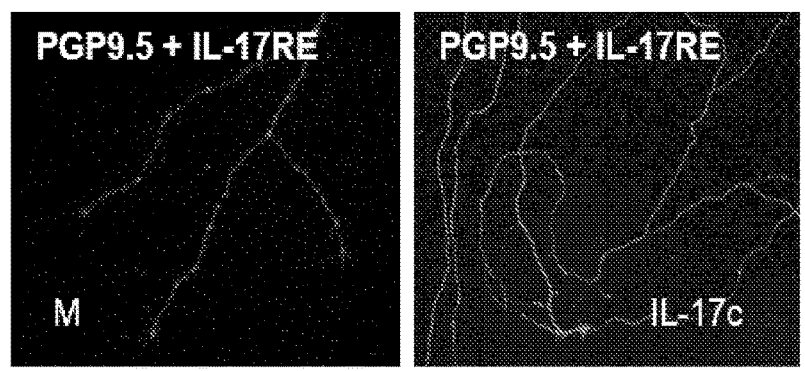
Figure 9H:
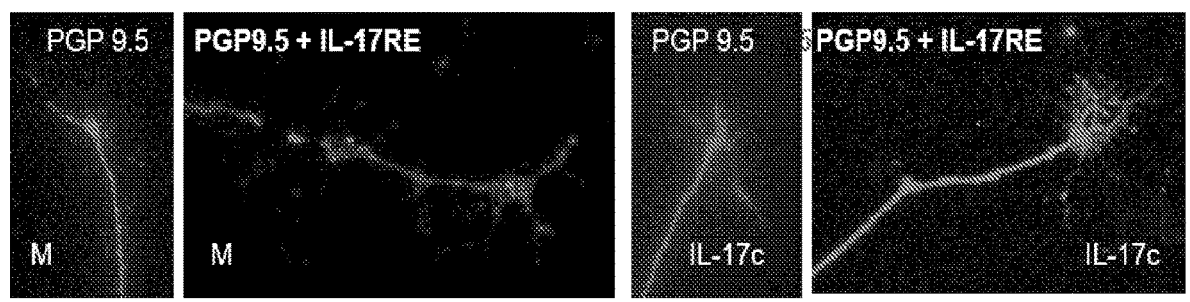

Next, human sensory neurons (HSN) were isolated from fetal DRG. HSN were cultured in full neural medium or such medium with IL-17c or NGF for 3 days before the cells were live imaged to measure neurite length, branch points and cell body area hourly for 16 hours (FIGS. 9A, 10A, 10B, 10C). Neurites grew longer and faster with more branches in the presence of IL-17c as compared to culture medium alone or medium plus NGF; In contrast, the growth rate of cell body were similar in all three conditions during the 16 hr time period (FIGS. 9B & 9C). To measure the effect of IL-17c on directional neurite growth, a 3-chamber microfluidic device was used with HSN placed in the middle channel and the left and right channels contained full medium (left) and full medium plus IL-17c (right), respectively (FIG. 9D). By day 10 significantly more neurites grew into the IL-17c containing channel than into the medium alone channel. On day 16, cells were fixed and stained with PGP9.5 and IL-17RE antibodies. Compared to those in the channel with medium alone, almost twice as many neurites were found in the IL-17c containing channel with 2.7-fold longer total neurites and 3.5-fold more branch points (FIGS. 9E & 9F). Neurites in the IL-17c channel were IL-17RE+ and appeared to have larger growth cones compared with those in the medium alone channel (FIGS. 9G & 9H). Taken together, the data suggest that IL-17c might be a neurotrophic factor promoting neurite growth and branching for HSN.

Figure 11A:
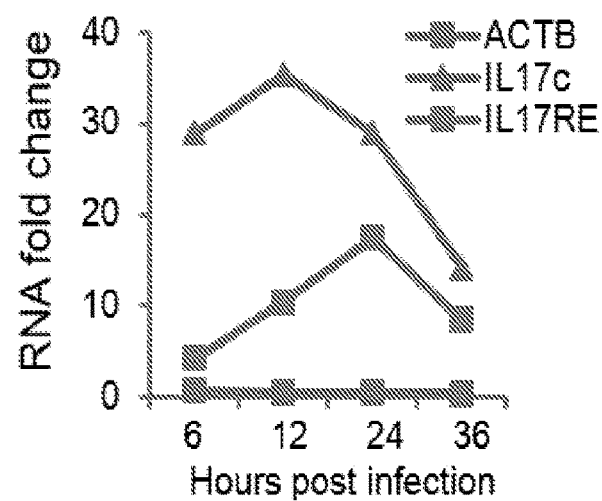
Figure 11B:
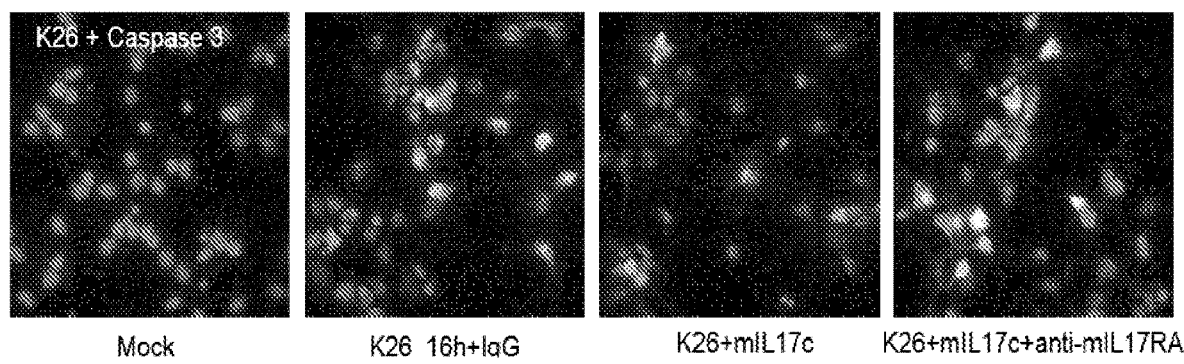
Figure 11C:
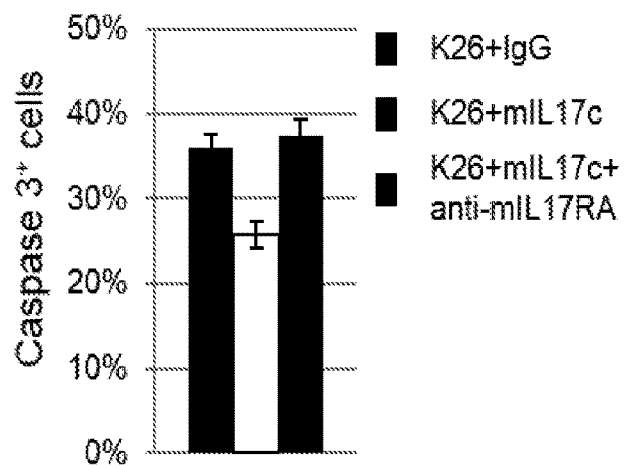

Pre-treatment with IL-17c reduces apoptosis during HSV infection of murine primary neurons and human primary keratinocytes. As a previous study indicated that IL-17c provides a survival signal for colon epithelial cells in a mouse intestinal tumor model (Song et al., 2014), tests were performed to determine if IL-17c has an anti-apoptotic effect on neurons. During a time course of HSV-1 (K26) infection of mouse primary cortical neurons (MCN), IL-17c was consistently induced throughout the time course as compared to mock infected cells; IL-17RE was also induced (FIG. 11A). Consistent with the gene expression pattern seen in laser captured keratinocytes in skin (FIG. 2B), IL-17a expression was not detected by quantitative RT-PCR in MCN (data not shown). Because the receptor for IL17c is a heterodimer of IL-17RE/IL-17RA, IL-17c signaling was blocked using a neutralizing antibody for IL-17RA, which had no significant effect on HSV gene expression (FIG. 12). Next, tests were performed to determine if pre-treatment with internally-generated Hutch exogenous murine IL-17c (mIL-17c) could aid in survival of neurons during HSV infection. Decreased levels of cleaved caspase 3 were detected by immunofluorescence when MCN were pre-treated with mIL-17c, and the presence of a murine IL-17RA neutralizing antibody (anti-mIL17RA) eliminated this reduction (FIGS. 11B & 11C). At 16 hours p.i, there was a 29% reduction of neurons undergoing apoptosis with mIL-17c pre-treatment before infection (FIG. 11C). There was no significant difference of cleaved caspase 3 profiles in neurons treated with control IgG or anti-mIL17RA (data not shown). Consistent with these results, use of internally-generated Hutch human IL-17c demonstrated an anti-apoptotic effect in human keratinocytes.

Figure 11D:
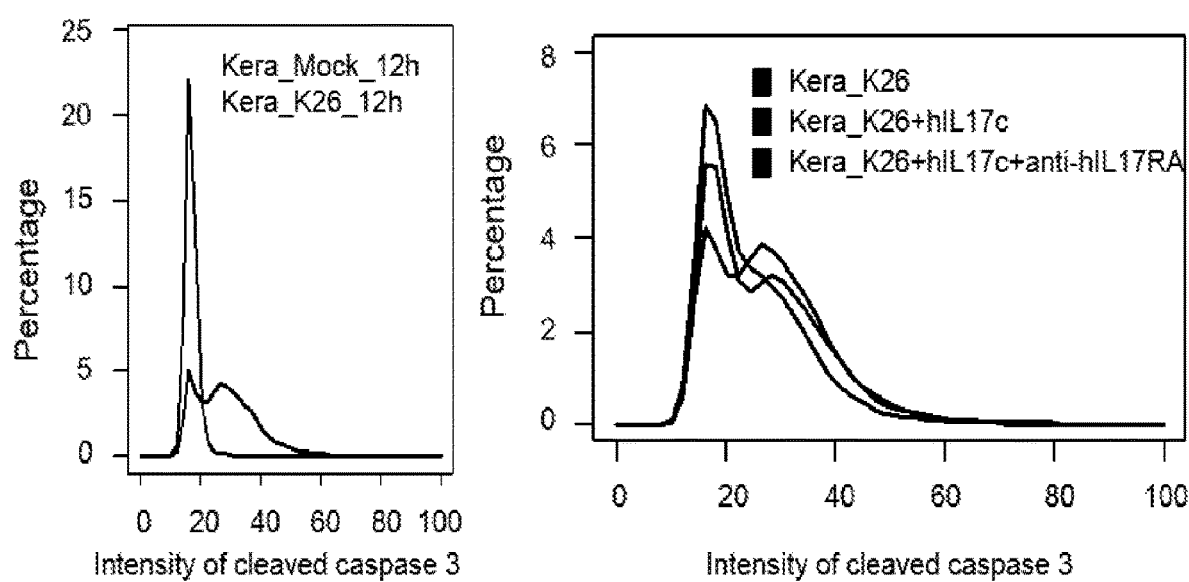

Because it has already been shown that HSV infection in human primary keratinocytes induces IL-17c and such cells have a high level of expression of IL-17c receptors (IL-17RA and IL-17RE) (FIGS. 5 and 7), it was next determined whether exogenous human IL-17c (hIL17c) pre-treatment provides a pro-survival signal to K26 infected keratinocytes. Indeed, pre-treatment of keratinocytes with hIL-17c reduced apoptosis during K26 infection and this was reversed in the presence of a neutralizing antibody for human IL-17RA (anti-hIL17RA) (FIG. 11D). Furthermore, blocking endogenous IL-17c signaling with neutralizing antibodies for IL-17RA during HSV infection of neurons and keratinocytes induced more apoptosis (data not shown). These findings suggest that IL-17c treatment provides a survival signal to both neurons and keratinocytes during HSV infection.

Discussion Target derived factors such as brain-derived neurotrophic factor (BDNF) and NGF have been described to regulate neuronal cell function, including cell survival, axonal growth and guidance, through retrograde signaling (Harrington and Ginty, 2013; Tessier-Lavigne and Goodman, 1996). Here, a novel functional interaction between mucosal keratinocytes and peripheral sensory neurons through the IL-17c/IL-17RE pathway is described. The in vivo data clearly demonstrate that there is peripheral nerve growth during both clinical and subclinical HSV reactivation. The findings that HSV infection induces IL-17c in keratinocytes, the receptor for IL-17c is expressed on skin nerve endings located at the site of reactivation, blocking IL-17c during HSV infection induces neuronal apoptosis, and exogenous IL-17c induces neurite show that this keratinocyte-peripheral nerve interaction is a the mechanism behind the in vivo observations. One of the intriguing aspects of the data is the demonstration that nerve growth was observed over a prolonged 4-8 week time period post reactivation. The exact mechanism behind this prolonged effect remains to be determined; however in affected areas there is evidence for frequent if not constant release of HSV-2 into the mucosal tissue, potentially providing the stimulus for prolonged IL-17c production in keratinocytes locally (Schiffer, 2010).

From a virus point of view, IL-17c may provide an increased opportunity for HSV to reach more neurons for establishing latent infection and later to gain more access to peripheral targets during viral reactivation. Interestingly, HSV-2 glycoprotein G has recently been proposed to regulate growth of free nerve endings in a mouse infection model (Cabrera et al., 2015). From the host point of view, neuron survival and growth helps preserve sensory nerve function. This mutually beneficial interaction provides a mechanism for the lack of hypoesthesia associated with recurrent HSV infections and potentially explain the long standing controversy on how HSV infection can impair peripheral nerve endings and yet not result in any clinically discernible long standing effect on peripheral nerve function.

Both HSV-1 and HSV-2 are neurotrophic viruses that likely replicate in neurons before establishment of latency; little is known about the role of neurotropic factors in HSV reactivation in humans. The in vitro data suggest that HSV infection in HSN in vivo would induce the expression of IL-17c, which in turn offers a survival signal to neurons in autocrine and paracrine manners. Skin keratinocytes also produce IL-17c during HSV infection at peripheral sites, providing protection from apoptosis through a similar mechanism. IL-17RA is ubiquitously expressed and it is a shared receptor for IL-17a, IL-17c, IL-17e and IL-17f (Gaffen, 2009; Pappu et al., 2012). It is shown that the anti-apoptotic effect of IL-17c in both keratinocytes and neurons can be completely blocked by IL-17RA neutralizing antibodies, suggesting that IL-17RA is required for the anti-apoptotic effect of IL-17c in both cell types. IL-17RE expression can be detected in nerve endings of skin biopsies during HSV-2 recurrent infection and in both cell bodies and axons in human fetal DRGs. Taken together, it is proposed that IL-17c from keratinocytes could bind to its receptors (IL-17RA/IL-17RE) on nerve endings and protect axons and cell bodies through retrograde signaling. In recent studies it was demonstrated that IL-17c and IL-17RE and IL-17RA exist as a trimer, providing further evidence that these in vitro observations are operant in vivo (data not shown).

The ex vivo data clearly indicate that IL-17c can result in both peripheral nerve growth and guidance. The molecular mechanisms by which IL-17c promulgates neuronal growth are as yet unclear. Nerve regeneration/repair is a tightly coordinated molecular and cellular process that involves numerous different cell types. The normal peripheral nerve trunk comprises complex, highly organized structures such as the endoneurium that contain axons, Schwann cells, macrophages, fibroblasts and blood vessels. In addition, a mixture of inflammatory cells infiltrate to sites of nerve injuries, adding further complexity to this microenvironment (Cattin et al., 2015; Zochodne, 2008). In the context of recurrent HSV-2 infection in humans, the IL-17c/IL-17RE pathway provides crosstalk between mucosal keratinocytes and peripheral sensory neurites that aids in nerve repair.

In summary, this Example demonstrates that keratinocytes produce IL-17c, which stimulates nerve growth, for example during recurrent HSV-2 infection in humans.

Example 2

Paclitaxel and vincristine have been used in the literature for mouse studies on peripheral nerve damages and these literature procedures will be followed (Neurobiology of Disease 2006, Melli G; Brain research 1997, Contreras PC). Paclitaxel and vincristine will be injected through tail vein at a concentration of 1 to 25 mg/Kg weight.

>50 mg of murine IL-17c will be prepared for mouse experiments. For local administration, IL-17c will be delivered by topical cream or patch at one flank in mouse back skin. For systematic administration, IL-17c will be delivered by intraperitoneal injection at a concentration of 1 to 10 mg/Kg weight.

TABLE 1

Experimental design for IL-17c treatment prevention of chemotherapeutic drug induced peripheral neuropathy in mice.

| Route | Neurotrophic factor or carrier control Local or systematic | Chemotherapeutic drugs or vehicles Intravenous |
|---|---|---|
| Day 1 | IL-17c or PBS | |
| Day 2 | IL-17c or PBS | Paclitaxel or Cremophor Vincristine Or PBS |
| Day 3 | IL-17c or PBS | |
| Day 4 | IL-17c or PBS | Paclitaxel or Cremophor Vincristine Or PBS |
| Day 5 | IL-17c or PBS | |
| Day 6 | IL-17c or PBS | Paclitaxel or Cremophor Vincristine Or PBS |
| Day 7 | IL-17c or PBS | |
| Day 8 | IL-17c or PBS | |
| Day 9 | IL-17c or PBS | |
| Day 10 | IL-17c or PBS | |
| Day 11 | IL-17c or PBS | |
| Day 12 | IL-17c or PBS | |

Beneficial effects against neuropathy will be observed.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the promotion of neural growth and neural survival as measured by axon growth, axon guidance in a particular direction, or neural cell survival in comparison to a relevant control condition.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, where references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

SHORT-CITE REFERENCE LIST

Abemayor and Sidell. 1989. Environmental health perspectives 80:3-15.
Cabrera, et al., 2015. Secreted herpes simplex virus-2 glycoprotein G modifies NGF-TrkA signaling to attract free nerve endings to the site of infection. PLoS pathogens 11:e1004571.
Cattin, et al., 2015. Cell 162:1127-1139.
Chang, et al., 2011. Immunity 35:611-621.
Chuong et al., 2002. Experimental dermatology 11:159-187.
Cuchet, et al., 2011. Journal of cell science 124:280-291.
Dev, et al., 2011. Current topics in microbiology and immunology 349:115-143.
Gaffen, 2009. Nature reviews. Immunology 9:556-567.
Gaffen, 2011. Current opinion in immunology 23:613-619.
Harrington and Ginty. 2013. Nature reviews. Neuroscience 14:177-187.
Honda and Taniguchi. 2006. Nature reviews. Immunology 6:644-658.
Johnston, et al., 2013. Journal of immunology 190:2252-2262.
Johnston, et al., 2012. Lancet 379:641-647.
Koutsky, et al., 1992. The New England journal of medicine 326:1533-1539.
Lloyd, et al., 1995. The Journal of cell biology 129:1329-1344.
Misery, 1997. The British journal of dermatology 137:843-850.
Orzalli, et al., 2012. Proceedings of the National Academy of Sciences of the United States of America 109:E3008-3017.
Pappu, et al., 2012. Trends in immunology 33:343-349.
Peng, et al., 2009. Journal of virology 83:12559-12568.
Peng, et al., 2012. Journal of virology 86:10587-10596.
Ramirez-Carrozzi, et al., 2011. Nature immunology 12:1159-1166.
Roizman and Whitley, 2013. Annual review of microbiology 67:355-374.
Schiffer et al., 2010. Proceedings of the National Academy of Sciences of the United States of America 107:6.
Schiffer, et al., 2013. Rapid localized spread and immunologic containment define Herpes simplex virus-2 reactivation in the human genital tract. eLife 2:e00288.
Song, et al., 2014. Immunity 40:140-152.
Song, et al., 2011. Nature immunology 12:1151-1158.
Tessier-Lavigne and Goodman, 1996. Science 274:1123-1133.
Wald, et al., 1997. J Clin Invest 99:1092-1097.
Zhu, et al., 2009. Nat Med 15:886-892.
Zhu, et al., 2007. The Journal of experimental medicine 204:595-603.
Zhu, et al., 2013. Nature 497:494-497.
Zochodne, 2008. Neurobiology of Peripheral Nerve Regeneration. Cambridge University Press.

What is claimed is:

1. A method of promoting neural growth and/or neural survival in a subject in response to a herpes simplex virus (HSV) viral infection, the method comprising administering to the subject a therapeutically effective amount of an IL-17c protein thereby promoting neural growth and/or neural survival in the subject.

2. The method of claim 1, wherein the neural growth is evidenced by nerve density, neurite growth and/or neurite guidance.

3. The method of claim 1, wherein the IL-17c protein comprises SEQ ID NO: 1.

4. The method of claim 1, wherein the promoted neural growth and/or neural survival is found in a sensory or motor neural cell and/or nerve.

5. The method of claim 4, wherein the administering is in or around a site of the sensory or motor neural cell and/or nerve.

6. The method of claim 1, wherein the administering is topical.

7. The method of claim 1, wherein the administering is through application of a transdermal patch.

8. The method of claim 1, wherein the administering is prophylactic.

9. The method of claim 1 wherein the promoting alleviates a symptom of neurodegeneration.

10. The method of claim 9 wherein the neurodegeneration is a peripheral neuropathy.

11. A method of promoting neural growth and/or neural survival in response to a herpes simplex virus (HSV) viral infection, the method comprising contacting a neural cell or nerve with a therapeutically effective amount of an IL-17c protein thereby promoting neural growth and/or neural survival.

12. The method of claim 11, wherein the neural growth and/or neural survival is evidenced by increased neural cell survival, increased neurite growth, neurite guidance, and/or increased innervation.

13. The method of claim 11, wherein the IL-17c protein comprises SEQ ID NO: 1.

14. The method of claim 11, wherein the neural cell or nerve is from:

the peripheral nervous system; and/or a sensory or motor neural cell or nerve; and/or within the dermis of a subject.

15. The method of claim 14, wherein the subject is a subject in need of the promoting neural growth and/or neural survival.

16. A method of reducing and/or delaying chemotherapy-associated neuron apoptosis in a cell in vitro, comprising:

administering to the cell in vitro, before a dose of chemotherapy, a therapeutically effective amount of an IL-17c protein, thereby reducing and/or delaying chemotherapy-associated neuron apoptosis in the cell.

17. The method of claim 16, wherein the IL-17c protein comprises SEQ ID NO: 1.

* * * * *